(12) United States Patent
Lin et al.

(10) Patent No.: US 11,027,260 B2
(45) Date of Patent: Jun. 8, 2021

(54) LOW PRESSURE NANOWIRE MEMBRANE FOR CATALYTIC REACTIONS AND METHODS OF MAKING AND USING THE SAME

(71) Applicant: UCHICAGO ARGONNE, LLC, Chicago, IL (US)

(72) Inventors: Xiao-Min Lin, Naperville, IL (US); Jiangwei Wen, Lemont, IL (US); Kun Wu, Naperville, IL (US); Jun Tian, Lemont, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 0 days.

(21) Appl. No.: 16/275,047

(22) Filed: Feb. 13, 2019

(65) Prior Publication Data
US 2020/0254426 A1 Aug. 13, 2020

(51) Int. Cl.
*B01J 23/89* (2006.01)
*B01J 35/02* (2006.01)
*B01J 35/06* (2006.01)
*B01J 35/10* (2006.01)
*B01J 35/00* (2006.01)
*B01J 37/02* (2006.01)
*C07D 249/04* (2006.01)

(52) U.S. Cl.
CPC ....... *B01J 23/8926* (2013.01); *B01J 35/0013* (2013.01); *B01J 35/023* (2013.01); *B01J 35/065* (2013.01); *B01J 35/10* (2013.01); *B01J 37/0215* (2013.01); *B01J 37/0236* (2013.01); *C07D 249/04* (2013.01)

(58) Field of Classification Search
CPC ......... B01J 35/023; B01J 35/06; B01J 35/065
See application file for complete search history.

(56) References Cited

U.S. PATENT DOCUMENTS

| | | | |
|---|---|---|---|
| 7,922,787 B2 | 4/2011 | Wang et al. | |
| 8,865,715 B2 | 10/2014 | Dorsch et al. | |
| 9,103,654 B1* | 8/2015 | Cox | G01B 7/14 |
| 9,315,468 B2 | 4/2016 | Boons et al. | |
| 9,790,398 B2 | 10/2017 | Carter et al. | |
| 9,879,044 B2 | 1/2018 | Hill et al. | |

(Continued)

FOREIGN PATENT DOCUMENTS

| | | |
|---|---|---|
| EP | 2751125 B1 | 6/2015 |
| EP | 3146068 A1 | 3/2017 |

OTHER PUBLICATIONS

Ho, M.D. et al—Fractal Gold Nanoframework for Highly Stretchable Trasnparent Strain-Insensitive Conductors—Nanoletters, May 16, 2018, 18, 3593-3599 (Year: 2018).*

(Continued)

*Primary Examiner* — Bradley R Spies
(74) *Attorney, Agent, or Firm* — Marshall, Gerstein & Borun LLP

(57) ABSTRACT

In embodiments a metal or metal alloy nanowires are assembled into a nanoporous membrane that can be used in methods for catalyzing various reactions under low pressures and achieving high flow rate of the reactions. In embodiments, the membranes of the disclosure can catalyze CuAAC reactions with high efficiency and minimum leaching of active Cu species.

14 Claims, 30 Drawing Sheets

(56) References Cited

U.S. PATENT DOCUMENTS

| | | | | |
|---|---|---|---|---|
| 2010/0086604 | A1* | 4/2010 | Stellacci | B01J 20/3289 |
| | | | | 424/489 |
| 2011/0275005 | A1* | 11/2011 | Zhu | B82Y 30/00 |
| | | | | 429/482 |
| 2013/0165728 | A1* | 6/2013 | Zurcher | C01F 5/08 |
| | | | | 585/658 |
| 2016/0206754 | A1 | 7/2016 | Chang et al. | |
| 2017/0297008 | A1 | 10/2017 | Zeng | |
| 2018/0059541 | A1 | 3/2018 | Campbell et al. | |

OTHER PUBLICATIONS

Gordon, E. B. et al—Application of Au—CU nanowires fabricated by laser ablation in superfluid helium as catalysts for CO oxidation— Springer, Oct. 29, 2015 (Year: 2015).*

Ahlquist et al., Enhanced Reactivity of Dinuclear Copper(I) Acetylides in Dipolar Cycloadditions, Organometallics, 26(18):4389-91 (2007).

Alonso et al., Copper Nanoparticles in Click Chemistry, Acc. Chem. Res., 48(9):2516-28 (Sep. 2015).

Bai et al., A Highly Efficient Single-Chain Metal-Organic Nanoparticle Catalyst for Alkyne-Azide "Click" Reactions in Water and in Cells, J. Am. Chem. Soc., 138:11077-80 (Sep. 2016).

Banan et al., Copper immobilized onto polymer-coated magnetic nanoparticles as recoverable catalyst for 'click' reaction, Applied Organometallic Chem., 31(5):e3604 (May 2017).

Bari et al., Simple hydrothermal synthesis of very-long and thin silver nanowires and their application in high quality transparent electrodes, J. Mater. Chem. A, 4, 11365-11371, (2016).

Baxendale et al., Multistep synthesis using modular flow reactors: Bestmann-Ohira reagent for the formation of alkynes and triazoles, Angew. Chem. Int. Ed. Engl., 48(22):4017-21 (2009).

Bebensee et al., On-surface azide-alkyne cycloaddition on Cu(111): does it "click" in ultrahigh vacuum?, J. Am. Chem. Soc., 135(6):2136-9 (Feb. 2013).

Biesinger, Advanced analysis of copper X-ray photoelectron spectra, Surace and Interface Analysis, 49(13):1325-34 (Dec. 2017).

Borah et al., Stabilization of Cu(0)-nanoparticles into the nanopores of modified montmorillonite: An implication on the catalytic approach for "Click" reaction between azides and terminal alkynes, Green Chem., 13:3453-60 (2011).

Ceylan et al., Chemical synthesis with inductively heated copper flow reactors, Synlett, 13:2009-13 (2010).

Chassaing et al., When CuAAC 'Click Chemistry' goes heterogeneous, Catal. Sci. Technol., 6:923-57 (2016).

Cook et al., An Organometallic Cu20 Nanocluster: Synthesis, Characterization, Immobilization on Silica, and "Click" Chemistry, J. Am. Chem. Soc., 140(1):394-400 (Jan. 2018).

Decan et al., Copper nanoparticle heterogeneous catalytic 'click' cycloaddition confirmed by single-molecule spectroscopy, Nat. Commun. 5:4612 (2014).

Dedola et al., Synthesis of alpha- and beta-D-glucopyranosyl triazoles by CuAAC 'click chemistry': reactant tolerance, reaction rate, product structure and glucosidase inhibitory properties, Carbohydr. Res., 345(9):1123-34 (Jun. 2010).

Deraedt et al., Recyclable catalytic dendrimer nanoreactor for part-per-million Cu(I) catalysis of "click" chemistry in water, J. Am. Chem. Soc., 136(34):12092-8 (Aug. 2014).

Dervaux et al., Heterogeneous azide-alkyne click chemistry: towards metal-free end products, Chem. Sci., 3:959-66 (2012).

Diaz Arado et al., On-Surface Azide-Alkyne Cycloaddition on Au(111), ACS Nano, 7(10):8509-15 (2013).

Dorner et al., A short route for the synthesis of "sweet" macrocycles via a click-dimerization-ring-closing metathesis approach, Chem. Commun. (Camb.), (22):2852-4 (Jun. 2005).

Ferreira et al., Synthesis, biological activity, and molecular modeling studies of 1H-1,2,3-triazole derivatives of carbohydrates as alpha-glucosidases inhibitors, J. Med. Chem., 53(6):2364-75 (Mar. 2010).

Fuchs et al., Mechanistic Insights into Copper(I)-Catalyzed Azide-Alkyne Cycloadditions using Continuous Flow Conditions, Adv. Synth. Catal., 352(2-3):323-8 (Feb. 2010).

Gawande et al., Cu and Cu-Based Nanoparticles: Synthesis and Applications in Catalysis, Chem. Rev., 116(6):3722-811 (Mar. 2016).

Gianatassio et al., Organic chemistry. Strain-release amination, Science, 351(6270):241-6 (Jan. 2016).

Girard et al., Reusable polymer-supported catalyst for the [3+2] Huisgen cycloaddition in automation protocols, Org. Lett., 8(8):1689-92 (Apr. 2006).

Haldón et al., Copper-catalysed azide-alkyne cycloadditions (CuAAC): an update, Org. Biomol. Chem., 13(37):9528-50 (Oct. 2015).

Hashemi et al., In situ prepared CuI nanoparticles on modified poly(styrene-co-maleic anhydride): an efficient and recyclable catalyst for the azide-alkyne click reaction in water, Transition Metal Chemistry, 39(5):593-601 (Aug. 2014).

Hudson et al., Magnetic copper-iron nanoparticles as simple heterogeneous catalysts for the azide-alkyne click reaction in water, Green Chem., 14:622-4 (2012).

Iha et al., Applications of orthogonal "click" chemistries in the synthesis of functional soft materials, Chem. Rev., 109(11):5620-86 (Nov. 2009).

Jewett et al., Cu-free click cycloaddition reactions in chemical biology, Chem. Soc. Rev., 39(4):1272-9 (Apr. 2010).

Jha et al., Synthesis of glucose-tagged triazolium ionic liquids and their application as solvent and ligand for copper(I) catalyzed amination, Tetrahedron Lett., 54(35):4738-41 (Aug. 2013).

Jin et al., Click Chemistry of Alkyne-Azide Cycloaddition using Nanostructured Copper Catalysts, ChemCatChem., 4(9):1217-29 (Sep. 2012).

Jin et al., Isolation of bis(copper) key intermediates in Cu-catalyzed azide-alkyne "click reaction", Sci. Adv., 1(5):e1500304 (Jun. 2015).

Kirschner et al., Phonon-Driven Oscillatory Plasmonic Excitonic Nanomaterials, Nano Lett., 18(1):442-8 (2018).

Kolb et al., Click Chemistry: Diverse Chemical Function from a Few Good Reactions, Angew. Chem. Int. Ed. Engl., 40(11):2004-21 (Jun. 2001).

Li et al., SiO2—NHC—Cu(I): an efficient and reusable catalyst for [3+2] cycloaddition of organic azides and terminal alkynes under solvent-free reaction conditions at room temperature, Tetrahedron, 64(48):10825-30 (Nov. 2008).

Liang et al., The copper(I)-catalyzed alkyne-azide cycloaddition (CuAAC) "click" reaction and its applications. An overview, Coord. Chem. Rev., 255(23-24):2933-45 (Dec. 2011).

Lipshutz et al., Heterogeneous Copper-in-Charcoal-Catalyzed Click Chemistry, Angew. Chem., 118(48):8415-8 (Dec. 2006).

Luz et al., Bridging homogeneous and heterogeneous catalysis with MOFs: "Click" reactions with Cu-MOF catalysts, J. Catalysis, 276(1):134-40 (2010).

Mandoli, Recent Advances in Recoverable Systems for the Copper-Catalyzed Azide-Alkyne Cycloaddition Reaction (CuAAC), Molecules, 21(9):1174 (2016).

Meldal et al., Cu-catalyzed azide-alkyne cycloaddition, Chem. Rev., 108(8):2952-3015 (Aug. 2008).

Moses et al., The growing applications of click chemistry, Chem. Soc. Rev., 36(8):1249-62 (Aug. 2007).

Personick et al., Selective Oxygen-Assisted Reactions of Alcohols and Amines Catalyzed by Metallic Gold: Paradigms for the Design of Catalytic Processes, ACS Catal., 7(2):965-85 (2017).

Rao et al., Inorganic nanowires, Prog. Solid State Chem. 31, 5-147, (2003).

Rostovtsev et al., A stepwise huisgen cycloaddition process: copper(I)-catalyzed regioselective "ligation" of azides and terminal alkynes, Angew. Chem. Int. Ed. Engl., 41(14):2596-9 (Jul. 2002).

Rubensson et al., Local electronic structure in simple alcohols studied in x-ray emission, J. Electron Spectroscopy and Related Phenomena, 47:131-45 (1988).

Sarkar et al., PVP-Stabilized Copper Nanoparticles:? A Reusable Catalyst for "Click" Reaction between Terminal Alkynes and Azides in Nonaqueous Solvents, J. Phys. Chem. C, 112(9):3334-40 (2008).

Shi et al, Obtaining ultra-long copper nanowires via a hydrothermal process, Sci. Technol. Adv. Mater. 6, 761-765, (2005).

Shi et al., Facile Synthesis of Ultrathin AuCu Dimetallic Nanowire Networks, Eur. J. Inorg. Chem., 2012(16):2700-6 (Jun. 2012).

(56) References Cited

OTHER PUBLICATIONS

Sun et al., Uniform silver nanowires synthesis by deducing AgNO3 with ethylene glycol in the presence of seeds and poly(vinyl pyrrolidone), Chem. Mater. 14, 4736-4745, (2002).

Tasdelen et al., Light-induced copper(I)-catalyzed click chemistry, Tetrahedron Lett., 51(52):6945-7 (Dec. 2010).

Tiwari et al., Cu-Catalyzed Click Reaction in Carbohydrate Chemistry, Chem. Rev., 116(5):3086-240 (Mar. 2016).

Tornoe et al., Peptidotriazoles on solid phase: [1,2,3]-triazoles by regiospecific copper(i)-catalyzed 1,3-dipolar cycloadditions of terminal alkynes to azides, J. Org. Chem., 67(9):3057-64 (May 2002).

Tyler et al., Click chemistry enables preclinical evaluation of targeted epigenetic therapies, Science, 356(6345):1397-401 (Jun. 2017).

Varas et al., Copper(I)-catalyzed azide-alkyne cycloadditions in microflow: catalyst activity, high-T operation, and an integrated continuous copper scavenging unit, ChemSusChem., 5(9):1703-7 (Sep. 2012).

Wang et al., Heterogeneous Photocatalytic Click Chemistry, J. Am. Chem. Soc., 138(40):13127-30 (Sep. 2016).

Wang et al., Metal-catalyzed azide-alkyne "click" reactions: Mechanistic overview and recent trends, Coordination Chem. Rev., 316:1-20 (Jun. 2016).

Wen et al., Low-Pressure Flow Chemistry of CuAAC Click Reaction Catalyzed by Nanoporous AuCu Membrane, ACS Appl. Mater. Interfaces, 10(31):25930-5 (Aug. 2018).

Worrell et al., Direct evidence of a dinuclear copper intermediate in Cu(I)-catalyzed azide-alkyne cycloadditions, Science, 340(6131):457-60 (Apr. 2013).

Xi et al., Click Chemistry: Click Chemistry in Materials Science, Adv. Functional Mater., 24(18):2572-90 (May 2014).

Xu et al., In situ construction of three anion-dependent cu(i) coordination networks as promising heterogeneous catalysts for azide-alkyne "click" reactions, Inorg. Chem., 54(10):4737-43 (May 2015).

\* cited by examiner (a)

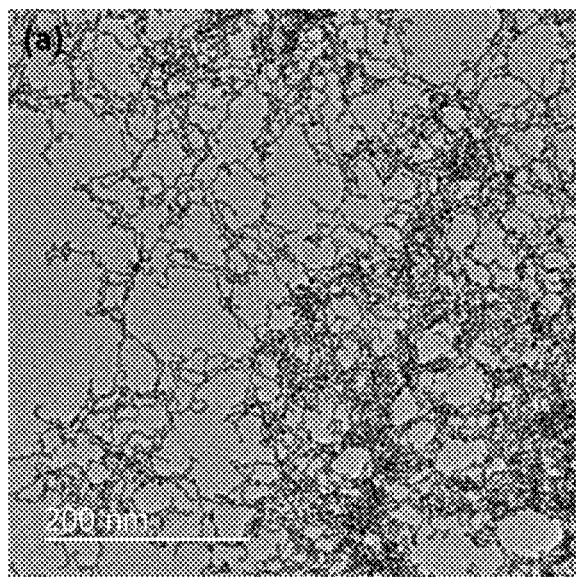
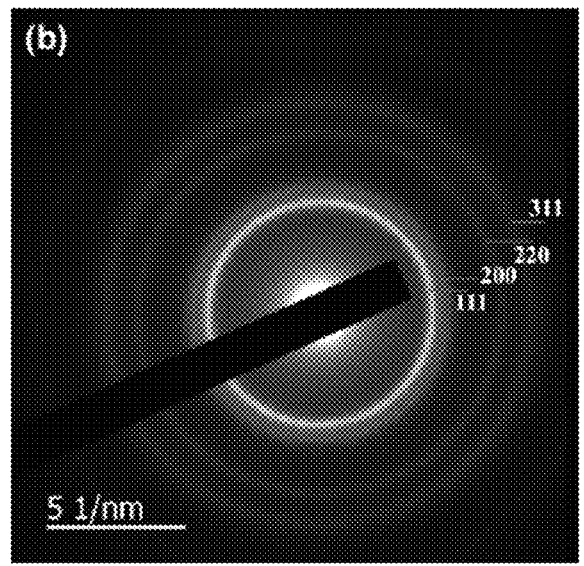
Fig. 2A Fig. 2B
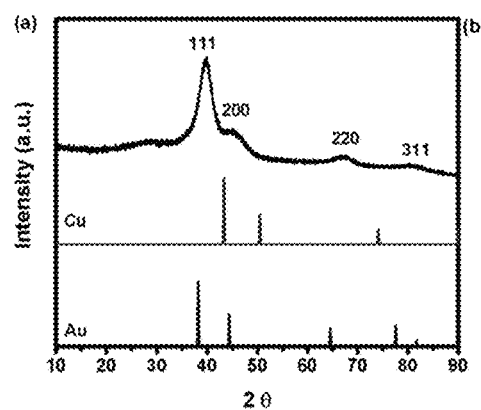
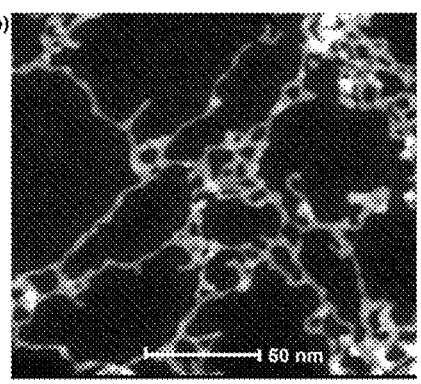
Fig. 3A Fig. 3B

| Experiment No. | Variation from the Standard Condition | Yield (%) |
|---|---|---|
| 1 | None | 96 |
| 2 | H$_2$O instead of EtOH | 86 |
| 3 | Au NWs instead of AuCu NWs | 0 |
| 4 | Au$_{1.3}$CuNWs instead of AuCu NWs | 80 |
| 5 | Au$_{0.66}$Cu NWs instead of AuCu NWs | 95 |
| 6 | Ar instead of air | 30 |

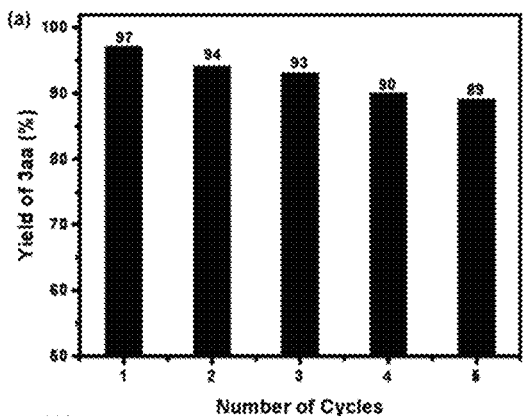
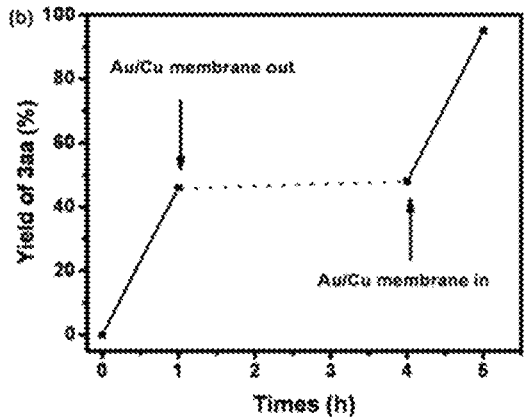
Fig. 6A
Fig. 6B
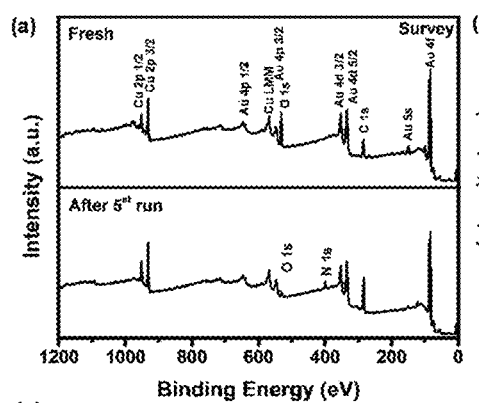
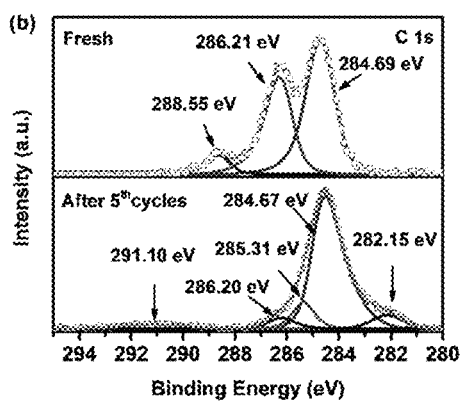
Fig. 7A
Fig. 7B

LOW PRESSURE NANOWIRE MEMBRANE FOR CATALYTIC REACTIONS AND METHODS OF MAKING AND USING THE SAME

STATEMENT OF GOVERNMENT SUPPORT

This invention was made with the support of under grant number DE-AC02-06CH11357 awarded by the Department of Energy. The US. Government has certain rights in this invention.

BACKGROUND

Field of the Disclosure

The disclosure generally relates to nanoporous membranes for catalyzing chemical reactions and methods of catalyzing chemical reactions under low pressure flow conditions using the nanoporous membranes.

Brief Description of Related Technology

Homogenous catalysts used in many chemical reactions face several challenges. A primary challenge is the difficulty and high cost of separating the catalyst from the reaction product. Heterogeneous catalysts, on the other hand, can generally be more easily recycled and reused. Conventional heterogeneous catalysts are designed by putting active metal species onto host materials, including polymer, oxide and carbon-based materials. The binding of active metal species with the host material could potentially alter the structure of metallic species, thereby affecting its catalytic activity. A weak binding between the catalyst and host materials also could cause gradual leaching of catalysts into reaction media, lead to gradual decrease of catalytic activity and the contamination of the reaction product, particularly under flow conditions.

Conventional heterogeneous catalysis systems typically include flow reactors coupled with efficient heterogeneous catalysts. An example is shown using a gravitational column packed with copper-based heterogeneous catalysts for 1,3-dipolar cycloaddition between azide and terminal alkyne (CuAAC) (U.S. Pat. No. 9,879,044 B2). CuAAC reaction belongs to a broad class of so-called click chemistry, in which chemical reaction is thermodynamically favorable to yield products with regio-specificity and stereo-specificity. As conventional heterogeneous catalysts for CuAAC reaction, copper (I) ions or Cu, $Cu_2O$ nanoparticles are typically grafted onto a series of host materials, including polymers, dendrimers, charcoal, mesoporous silica or zeolites, layered hydrotalcite, clays, polyoxometalates (POM) and metal-organic framework (MOF) solid materials. (C. Deraedt et al. J. Am. Chem. Soc. 136, 12092-12098 (2014); C. Girard et al., Org. Lett. 8, 1689-1692 (2006); B. H. Lipshutz et al., Angew. Chem. 118, 8415-8418, (2006)). Some of these catalysts show excellent conversion rates in CuAAC reaction, but under flow condition, significant amount of copper tends to leach out. (B. Dervaux et al. Chem. Sci. 3, 959-966, (2012); M. Fuchs et al., Adv. Synth. Catal. 352, 323-328 (2010)). Cu(0) NPs-catalyzed click reaction also requires the presence of triethylamine as a base to facilitate the conversion of Cu(0) to soluble Cu(I) species, which tends to accelerate the dissolution of active catalysts. Furthermore, organic contaminants in polymeric matrix and dissolved Cu(I) species are cytotoxic, which affect the purity of reaction product, and can be particularly detrimental for pharmaceutical compounds (A. Mandoli, Molecules, 21, 1174-1216, (2016)).

Leaching of the catalyst presents a significant problem for the pharmaceutical industry, where leached metal species affects the purity of the pharmaceutical compound. To overcome this problem, a conventional heterogeneous CuAAC flow reaction typically requires a downstream scavenging unit to purify the reaction product. (Varas et al. ChemSusChem 5, 1703-1707, (2012)), or carrying out the coupling reaction using metal-free approach (U.S. Pat. No. 9,315,468 B2). With these complex designs, many flow reactors need high pressure (up to 10-20 bar) to push the solvent through the catalyst column at a reasonable flow rate, and sometimes it is also necessary to maintain a high temperature in order to activate the catalyst.

SUMMARY

It is highly desirable for a variety of industries to utilize simpler, highly efficient and stable heterogeneous catalyst systems that can be operated under low pressure, continuous flow conditions.

In accordance with embodiments of the disclosure, a membrane for a catalyzing flow reactor can include metal-containing or metal-alloy containing nanowires self-assembled into a porous nanostructure, wherein the porous nanostructure has a thickness of about 10 nm to about 1 cm, and the nanowires have a diameter of about 1 nm to about 500 nm, and an aspect ratio of about 10 to about 100,000. In embodiments, the nanowires can be synthesized through solution chemistry. In embodiments, the nanostructure can be disposed on a porous support.

In accordance with embodiments, a method of making a catalytically active membrane can include depositing a solution comprising metal or metal-alloy containing nanowires in a surfactant onto a porous support; and drying the nanowires on the porous support by applying vacuum or pressurized air, wherein the nanowires self-assemble into a nanostructure on the porous support upon drying.

In accordance with embodiments, a method of making a catalytically active membrane can include depositing a solution comprising metal or metal-alloy containing nanowires and a surfactant onto an interface between immiscible liquids under conditions sufficient to allow the nanowires to self-assembly into a sheet at the interface; and subsequently transferring the sheet to a porous support to form the membrane.

In accordance with embodiments, a method of making a catalytically active membrane can include depositing a solution comprising metal or metal-alloy containing nanowires onto the surface of an immiscible liquid, evaporating the solvent under conditions sufficient to allow the nanowires to self-assembly into a sheet at the liquid-air interface; and transferring the sheet to a porous support to form the membrane.

In accordance with embodiments, a method of catalyzing a reaction under flow conditions can include flowing a solution comprising one or more reactants through a membrane in accordance with any of the embodiments herein, under a pressure of less than 10 bar and under conditions sufficient to catalyze a reaction of the one or more reactants. In embodiments, the reaction being catalyzed is the 1,3-dipolar cycloaddition between azide and terminal alkyne (CuAAC). In another embodiments, the reaction being catalyzed is the reduction of 4-nitrophenol to 4-aminophenol.

BRIEF DESCRIPTION OF THE DRAWINGS

FIG. 2A is a transmission electron microscopy (TEM) image of AuCu nanowires with branch structure in accordance with embodiments of the disclosure;

FIG. 2B is a selective area electron diffraction (SAED) pattern from a larger area of AuCu nanowires of FIG. 2A, The diffraction ring indicates that the nanowires have a polycrystalline nature;

FIG. 3A is an XRD analysis of the AuCu nanowires of FIG. 2A;

FIG. 3B is a high-angle annular dark-field scanning transmission electron microscopy (HAADF-STEM) image of the AuCu nanowires;

FIG. 6A is a graph showing the yield of 1,3-triazole compound obtained from reaction between phenylacetylene and benzyl azide in consecutive cycles using the same membrane catalyst but with fresh batch of reactants in accordance with embodiments of disclosure;

FIG. 6B is a schematic illustration of the experimental setup to test whether the reaction occurs at the membrane surface of membranes in accordance with embodiments of the disclosure or is promoted by the small amount of leached Cu species in solution.

FIG. 7A is graph showing XPS results of AuCu nanowires before and after CuAAC reactions performed in accordance with embodiments of the disclosure, surveying the entire range;

FIG. 7B is a graph showing the XPS results of FIG. 7A, in the C 1s region;

In FIGS. 7B-7D, circles are experimental data, and solid lines are fitting curves;

DETAILED DESCRIPTION

Figure 1A:
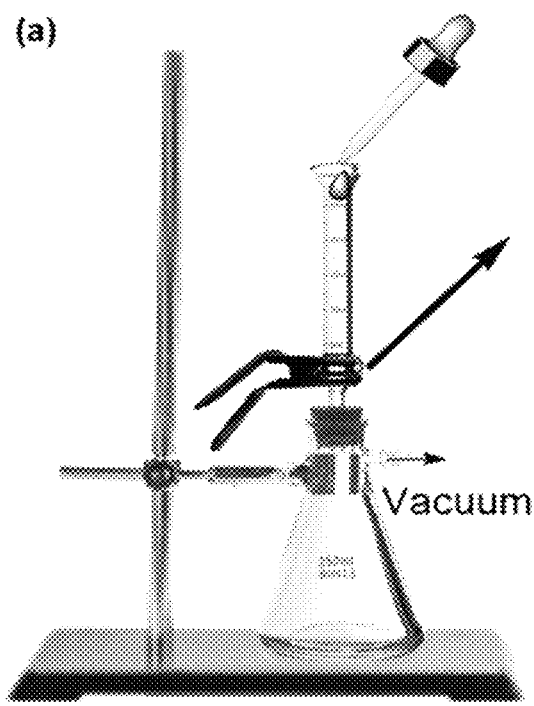
FIG. 1A is a schematic illustration of a method of preparing a catalytic membrane in accordance with embodiments of the disclosure.
Figure 1B:
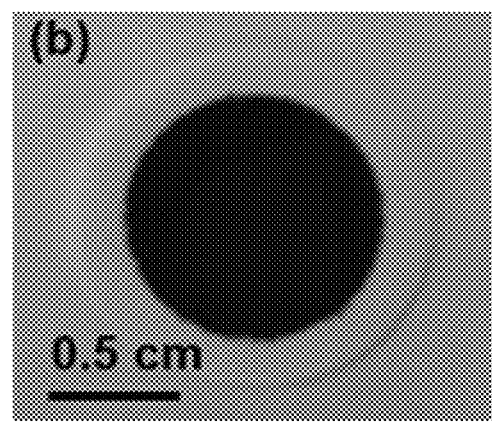
FIG. 1B is an optical image of a membrane in accordance with embodiments of the disclosure.
Figure 1C:
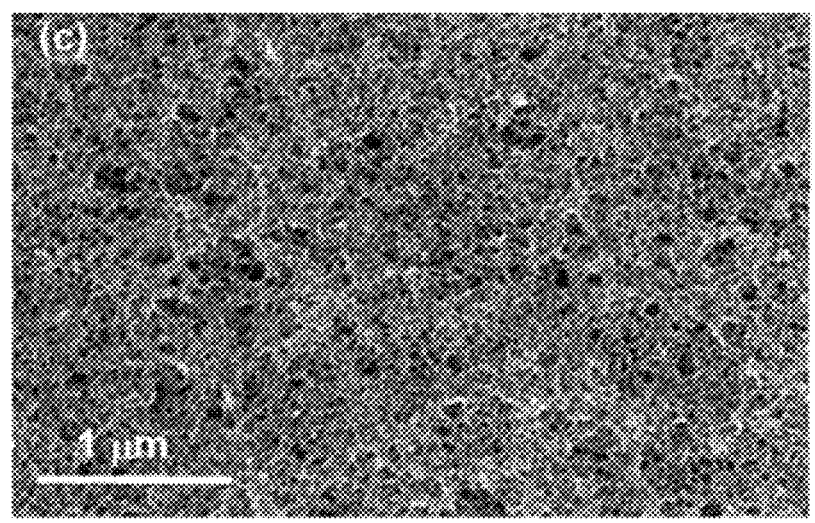
FIG. 1C is a scanning electron microscopy (SEM) image of the membrane made by the process illustrated in FIG. 1A.
Figure 1D:
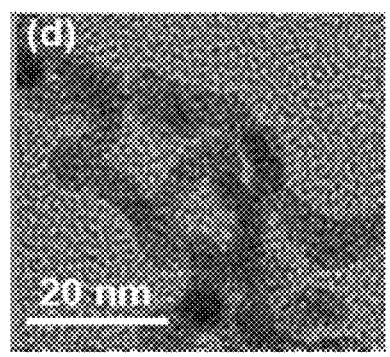
FIG. 1D is a transmission electron microscopy (TEM) image of the local structure of AuCu nanowire of FIG. 1C.
Figure 1E:
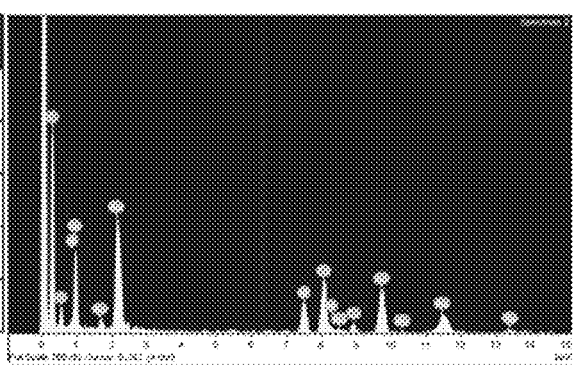
FIG. 1E is a table and graph illustrating the results of EDS analysis of the AuCu nanowires of FIG. 1C through transmission electron microscopy.

In accordance with embodiments of the disclosure a membrane comprising a metal or metal alloy based nanoporous nanostructure that can be used for catalyzing a number of different chemical reactions. In embodiments, the porous membrane can be formed through self-assembly of nanostructure building blocks. For example, in embodiments, the membrane can include a self-assembled porous structure of nanowires.

In accordance with embodiments, a method of flow reaction chemistry can include flowing a solution of reactants through a metal or metal alloy based nanoporous membrane to catalyze the reaction of the reactants, wherein the solution of reactants is flowed through the membrane at low pressure. For example, a pressure of less than 1 bar can be applied in some embodiments. In embodiments, the reaction can be performed at room temperature.

In accordance with embodiments, the membrane can have a composition of metals or metal alloys selected depending the reaction to be catalyzed. The membranes in accordance with the disclosure can be useful in a variety of applications for catalyzing a variety of different chemical reactions. For example, membranes in accordance with embodiments of the disclosure can be used as catalysts for click chemistry based on copper (I) catalyzed coupling reaction between azides and alkynes. For example, in embodiments, a nanostructure comprised of gold-copper alloy nanowires can be used in catalyzing 1,3-dipolar cycloaddition between azide and terminal alkyne (CuAAC). In embodiments, the methods of the disclosure can have a flow condition with pressure less than one bar. In embodiments, the membranes can be used in reactions performed at temperatures other than room temperature, so long as the temperature is below the sintering temperature of the nanostructure.

In embodiments, the reactants can be selected based on the reaction to be performed. For example, in embodiments, the reactants can include an azide and an alkyne. In embodiments, the azide and/or alkyne compounds can be extended to contain units of one or more of protein, peptide, amino acid, and carbohydrate.

For example, in accordance with embodiments of the disclosure, a membrane can be used in a method for performance of click reactions, wherein the membrane can function as a catalyst in a flow reactor. For example, a CuAAC click reaction can be performed in various embodiments. CuAAC is a quintessential click reaction that is carried out under mild conditions and yield chemospecific products. It has become one of the most reliable synthetic protocols in organic chemistry, material science and biomedical research. As an example, click chemistry has been widely used in bioconjugation (U.S. Pat. App. Pub. No. 2017/0297008), nucleic acid processing (EP2751125 B1, EP3146068 A1), polymeric coating and sealant (U.S. Pat. No. 9,790,398 B2), additive manufacturing inks (U.S. Pat. App. Pub. 2018/0059541), and the development of new anticancer drugs (U.S. Pat. No. 8,865,715 B2, U.S. Pat. App. Pub 2016/0206754).

Figure 4:
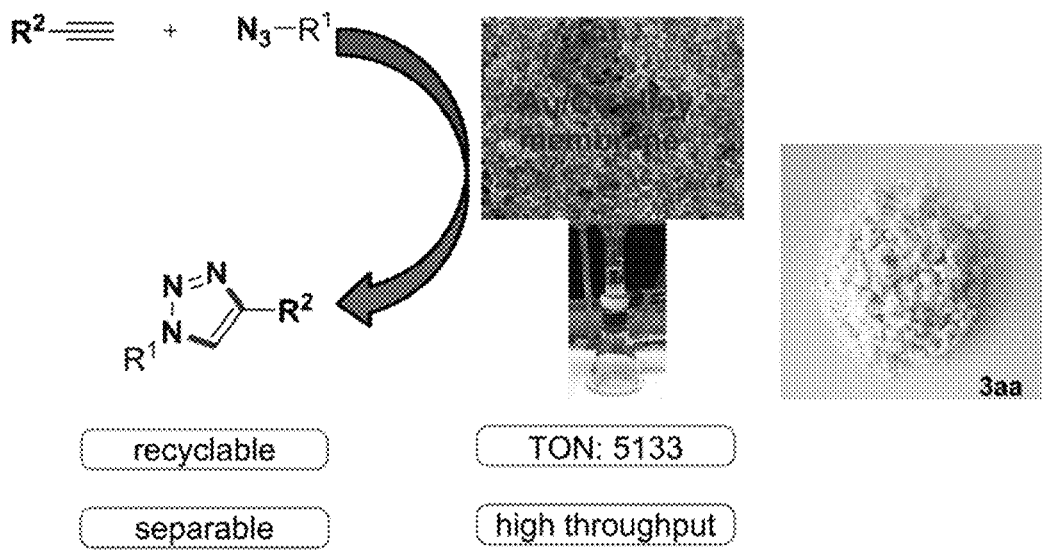
FIG. 4 is a schematic illustration of using AuCu membrane in flowing chemistry to catalyze CuAAC reaction between terminal alkynes and azides with high throughput, low pressure and reusable catalyst.

Referring to FIG. 4, in embodiments, a method of flow chemistry can include copper (I)-catalyzed 1,3 dipolar cycloaddition between azide and terminal alkyne (CuAAC) by flowing reactants through a membrane under low pressure. For example, in embodiments, the pressure can be less than 1 bar. In embodiments, the membrane is a AuCu nanowire containing membrane. In embodiments, the process can result performance of the CuAAC reaction without significant leaching of Cu species into the reaction medium.

In embodiments, a method of flow chemistry using membranes in accordance with embodiments of the disclosure can be used to catalyze chemical reactions that are performed at or close to room temperature. For example, FIG. 9 shows that reduction of 4-nitrophenol to 4-aminophenol catalyzed by AuCu nanowire membrane. Membranes and methods in accordance with embodiments of the disclosure can be used for a variety of chemical reactions and under various reaction conditions, so long at the reaction temperature is below the sintering temperature of the nanostructure component of the membrane.

In accordance with embodiments, the porous nanostructure membrane can include nanowires, nanoparticles, nanorods, and/or other nano-sized structures. For ease of reference, the collection of such nano-sized structures which can form the porous nanostructure will be referred to herein as nanostructure components. In various embodiments, the porous nanostructure includes nanowires. Referring to FIG. 2A, in embodiments, the nanowires can have branch or fractal-like structures, which can be useful as such nanowires are prone to form entangled network with high porosity.

In accordance with embodiments, the nanostructure can be a metal or metal alloy. In embodiments, the nanowire can include one or more of an elemental composition of coinage metals, Cu, Ag, Au, platinum-group metals, Ru, Rh, Pd, Os, Ir, Pt, other Group III to Group IIB transition metal, Sc, Ti, V, Cr, Mn, Fe, Co, Ni, Zn, Y, Zr, Nb, Mo, Tc, Cd, Hf, Ta, W, Re, Os, Ir, certain lanthanides La, Ce, Pr, Nd, Pm, Sm, Eu, Gd, Tb, and their various combination of alloy formed from elements listed above. The nanowire can also include one or more of metal carbide, nitride, chalcogenide, and oxide composition. Selection of the composition of the nanostructure can be tailored to the reaction to be catalyzed. For example, in embodiments, the nanostructure can include one or more of gold-copper nanowires. In embodiments, a metal alloy nanostructure can be used, as the incorporation of different types of metal can enhance the stability of active catalytic metal species. In embodiment, the metals of a metal alloy nanostructure can act cooperatively during the catalytic process.

In accordance with embodiments, the membrane can include a metal-alloy of various compositions. For example, in embodiments, the membrane can include a gold-copper alloy. In embodiments the Au/Cu molar ratio can be about 1:4 to 4:1, about 1:3 to about 3:1, about 1:2 to about 2:1.

Other suitable molar ratios of a gold-copper alloy include about 1:4, 1:3, 1:2, 1:1, 2:1, 3:1, and 4:1.

In embodiments, the nanostructure can include nanowires. Nanowires are one-dimensional nanostructures, with typical width on the order of 1-500 nm and the aspect ratio typically exceed 10. Nanowires can be made through various methods, including hydrothermal reactions (Bari et al. J. Mater. Chem. A, 4, 11365, (2016), U.S. Pat. No. 7,922,787 B2), chemical reduction of metal ions with a shape directing ligand (Wang Sun et al. Chem. Mater. 14, 4736-4745, (2002)); Vapor-liquid-solid (VLS) growth (Rao et al. Prog. Solid State Chem. 31, 5-147, (2003); Zhang et al. Eur. J. Inorg. Chem. 2012, 2700-2706). The nanowires or other nanostructure components for forming the membrane can be formed in accordance with known methods in the art.

In embodiments, the nanowires can be grown directly using solution synthesis. In embodiments, the nanowires can be grown from VLS and subsequently released from solid substrate and redissolved into solution to be used as starting materials. Because the aspect ratio of the nanowire is typically large, when the solvent is evaporated or filtered through an underlying porous substrate, nanowire can become easily entangled to form a membrane of a mesoporous network.

For example, in embodiments, alloy containing nanowires can be made in solution by co-reduction of metal salts. For example, a gold-copper nanowires can be formed in solution by co-reduction of the gold and copper salts by mixing gold chloride trihydrate ($HAuCl_4 \cdot 3H_2O$) and copper (II) dihydrate ($CuCl_2 \cdot 2H_2O$) with $NaBH_4$ and a surfactant. The surfactant can be for example Triton-X 100. Nanowires can be precipitated from the solution, for example, by gravitation force or a gentle centrifugation. Other known methods of making nanostructures can be used in the embodiments of the disclosure.

In embodiments, the nanostructure component can have a diameter or effective diameter of about 1 nm to about 500 nm, about 1 nm to about 5 nm, about 2 nm to about 8 nm, about 5 nm to about 50 nm, about 100 nm to about 500 nm, and about 50 nm to about 250 nm. Other suitable diameters include about 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 435, 450, 475, and 500 nm. In embodiments, the nanostructure component includes nanowires having a diameter of about 1 nm to about 500 nm. In embodiments, the nanostructure component incudes nanowires having a diameter of about 1 nm to about 5 nm.

In embodiments, the nanostructure components have an aspect ratio of in excess of 10. In embodiments, the nanostructure component has an aspect ratio of about 10 to about 100,000, about 10 to about 100, about 100 to about 500, about 1000 to about 5,000, about 10,000 to about 45,000, or about 50,000 to about 100,000, Other suitable aspect rations include, for example, about 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1500, 2000, 2500, 3000, 3500, 4000, 4500, 5000, 5500, 6000, 6500, 7000, 7500, 8000, 8500, 9000, 9500, 10,000, 20,000, 30,000, 40,000, 50,000, 60,000, 70,000, 80,000, 90,000, and 100,000.

In accordance with embodiments, the porous nanostructure can have a thickness or an average thickness of about 10 nm to about 1 cm, about 10 nm to about 100 nm, about 10 nm to about 50 nm, about 1 μm to about 100 μm, about 100 μm to 1 mm, about 1 mm to 1 cm, about 1 μm to about 10 μm, about 15 μm to about 45 μm, about 20 μm to about 80 μm, about 100 nm to about 1000 nm, about 200 nm to about 500 nm, and about 400 nm to about 750 nm. Other suitable thicknesses can include about 10 nm, 20 nm, 30 nm, 40 nm, 50 nm, 60 nm, 70 nm, 80 nm, 100 nm, 125 nm, 150 nm, 175 nm, 200 nm, 225 nm, 250 nm, 275 nm, 300 nm, 325 nm, 350 nm, 375 nm, 400 nm, 425 nm, 450 nm, 475 nm, 500 nm, 525 nm, 550 nm, 575 nm, 600 nm, 625 nm, 650 nm, 675 nm, 700 nm, 725 nm, 750 nm, 775 nm, 800 nm, 825 nm, 900 nm, 925 nm, 950 nm, 975 nm, 1 μm, 5 μm, 10 μm, 15 μm, 20 μm, 25 μm, 30 μm, 35 μm, 40 μm, 45 μm, 50 μm, 55 μm, 60 μm, 65 μm, 70 μm, 75, μm, 80 μm, 85, μm, 90 μm, 95 μm, 100 μm, 500 μm, 1000 μm, 1500 μm, 2000 μm, 2500 μm, 3000 μm, 3500 μm, 4000 μm, 4500 μm, 5000 μm, 5500 μm, 6000 μm, 6500 μm, 7000 μm, 7500 μm, 8000 μm, 8500 μm, 9000 μm, and 1 cm.

In embodiments, the relatively thin nature of the membranes in accordance with the disclosure can allow for efficient flow through of reactants at relatively low pressures. For example, methods in accordance with the disclosure can include application of a pressure of less than about 10 bar, less than about 5 bar, or less than about 1 bar for flow of the reactants through the membrane. For example, in embodiments, a pressure of about 0.1 bar to less than about 10 bar can be used. Other suitable pressures include about 0.1, 0.5, 1, 1.5, 2, 2.5, 3, 3.5, 4, 4.5, 5, 5.5, 6, 6.5, 7, 7.5, 8, 8.5, 9, 9.9, and less than 10 bar.

In various embodiments, the membrane can include a porous substrate upon which the nanostructure rests or is disposed. Various porous substrates can be used including, but not limited to, one or more of cellulose and chitosan-based filters, polycarbonate filters, active carbon filter, ceramic filter, polysulfone filter and polyamide filter.

In accordance with embodiments, the membrane can have nano-sized pores. For example, the membrane can have an average pore size in a range about 1 nm to about 500 nm, about 1 nm to 10 nm, about 50 nm to about 100 nm, about 100 nm to about 500 nm, about 20 nm to about 80 nm, about 15 nm to about 75 nm, about 70 nm to about 100 nm, about 30 nm to about 50 nm, and about 10 nm to about 65 nm. Other suitable average pore sizes include about 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, and 500 nm.

In embodiments, the membrane can have a porosity of about 20% to about 80%, about 20% to about 40%, about 30% to about 60%, about 20% to about 70%, about 50% to about 80%, and about 25% to about 75%. Other suitable porosity includes about 20, 25, 30, 35, 40, 45, 50, 55, 60, 65, 70, 75, and 80%.

Referring to FIG. 1A, in accordance with embodiments, a method of making the membrane can include forming the nanostructure component in solution, applying the solution to a porous substrate, and drying the nanostructure components on the porous substrate to form the membrane. For example, drying can be accomplished by using a vacuum to filter through the fluid of the nanostructure component solution. In embodiments, nanowires are prepared in solution and applied to a porous substrate. The fluid of the nanowire solution can be pulled through the porous substrate using a vacuum or other applied pressure, thereby drying the nanowires. Upon drying, the nanowires can become entangled into rope like structures and further entanglement of the rope like structures can occur to provide a porous nanostructure that interacts with a fluid as it passes through the nanostructure.

In embodiments, the method can include adding a solvent or chemical agents to a solution containing the nanowire component to induce precipitation of the nanowire component from the solution. For example, ethanol can be used to induce precipitation of a gold copper nanowire component in hexane solution.

In embodiments, the method can include depositing a solution of nanowires onto an immiscible liquid, and allowing nanowires to self-assemble to form a sheet at the liquid-liquid interface or upon solvent evaporation from a sheet at the liquid-air interface. The membrane thus formed can be transferred to other suitable supports using, for example, Langmuir trough deposition techniques.

As compared with bicontinuous, nanoporous metal substrates that are manufactured through dealloying of binary or ternary alloys, the membranes in accordance with embodiments of the disclosure eliminate the cumbersome dealloying process, which requires strong chemical etchants. Also, the membranes in accordance with embodiments of the disclosure have nanowires with diameters much smaller than the ligament size for dealloyed structure. This can advantageously provide higher active surface area for catalysis. In accordance with embodiments, the high surface area of the nanowires allow for thinner membranes to be used, which can result in reduction of the pressure needed for flow through process, and can allow flow chemistry processes to be performed at low pressure with high throughputs.

In embodiments, a nanowire based porous membrane in accordance with the disclosure can be used in methods of catalyzing a variety of chemical reactions, particularly green chemistry reactions. For example, membranes in accordance with embodiments of the disclosure can be used in catalyzing reactions that occur at or close to room temperature. For example, referring to FIG. 9, AuCu nanowire membranes in accordance with the disclosure can be used to catalyzed reduction of 4-nitrophenol to 4-aminophenol. In general, the application of these membrane could only be limited by the reaction temperature, in which high temperature could cause nanowire to sinter and irreversible structural change would occur.

EXAMPLES

Example 1: Method of Making Nanoporous Membrane

Au/Cu nanowires were synthesized by co-reduction of the precursors of gold and copper salts with $NaBH_4$ in an aqueous solution. For synthesis of AuCu nanowires with molar ratio of Au:Cu of 1:1, 50 ml of an aqueous solution containing 0.5 mM $HAuCl_4$, 0.5 mM $CuCl_2.2H_2O$, and 0.5 g/L Triton-100 X were added into an ice-cold 100 ml three-necked, round-bottom flask, and the mixture was stirred under argon for 30 minutes. A solution containing 10.4 mg $NaBH_4$ dissolved in 2 ml deionized water was quickly injected into the flask. The color of the solution turned immediately to black. After stirring for 1 min, the mixture was heated to 35° C. and maintained at 35° C. for 8 min without stirring. The product was precipitated from the solution and collected by centrifugation at 5000 rpm for 5 min.

The nanowires were then collected through filtering the nanowire solution using a polycarbonate filter membrane (Isopore™ 0.4 μm HTTP), thereby forming the nanoporous membrane on the polycarbonate substrate. The membrane was then washed 3 times with deionized water and ethanol, respectively.

Figure 3C:
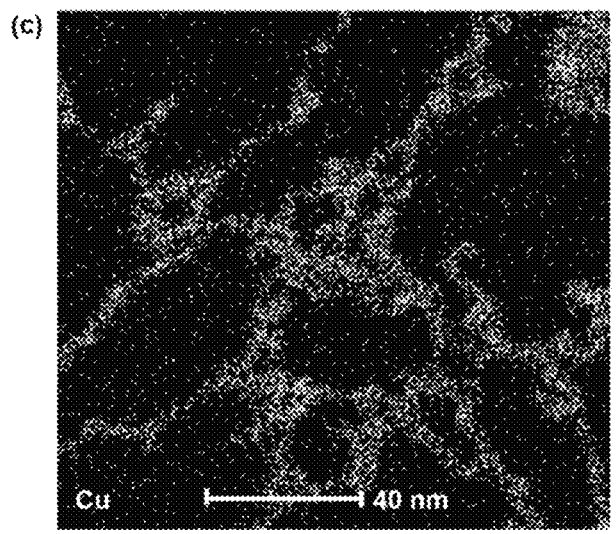
FIG. 3C is the elemental distribution of Cu mapped using scanning transmission electron microscopy (STEM-EDS mapping) in the same area of FIG. 3B.
Figure 3D:
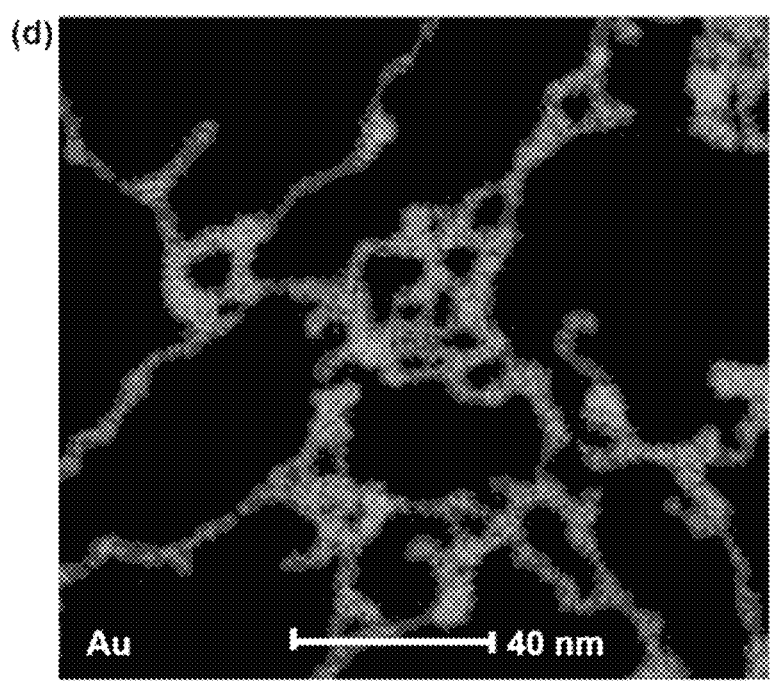
FIG. 3D is the elemental distribution of Au mapped in the same region as FIG. 3C. The molar ratio of these wires is Au/Cu=1:1.
Figure 11A:
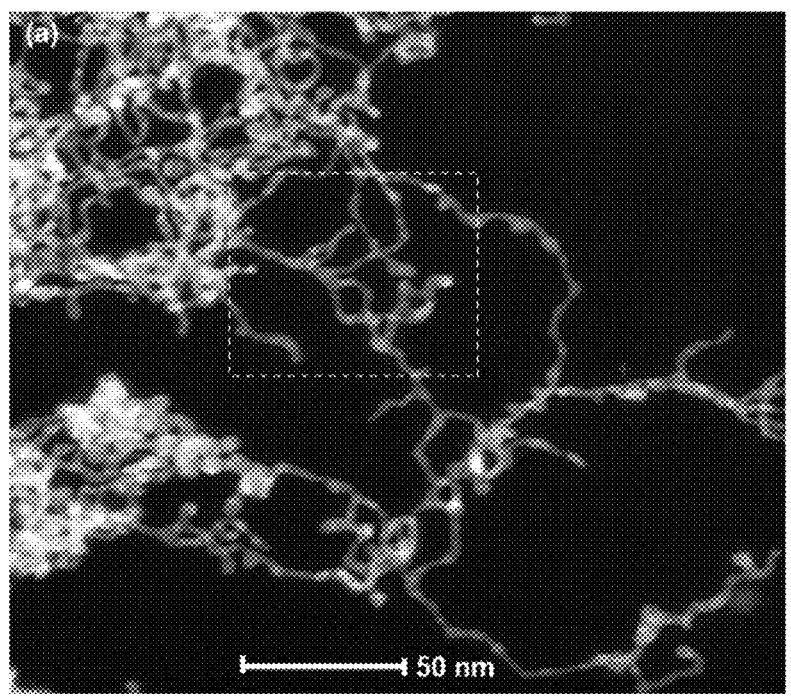
FIG. 11A is a HAADF-STEM image of an AuCu nanowire in accordance with embodiments of the disclosure after a $5^{th}$ cycle of click reaction, illustrating that the nanowire maintained its original morphology.
Figure 11B:
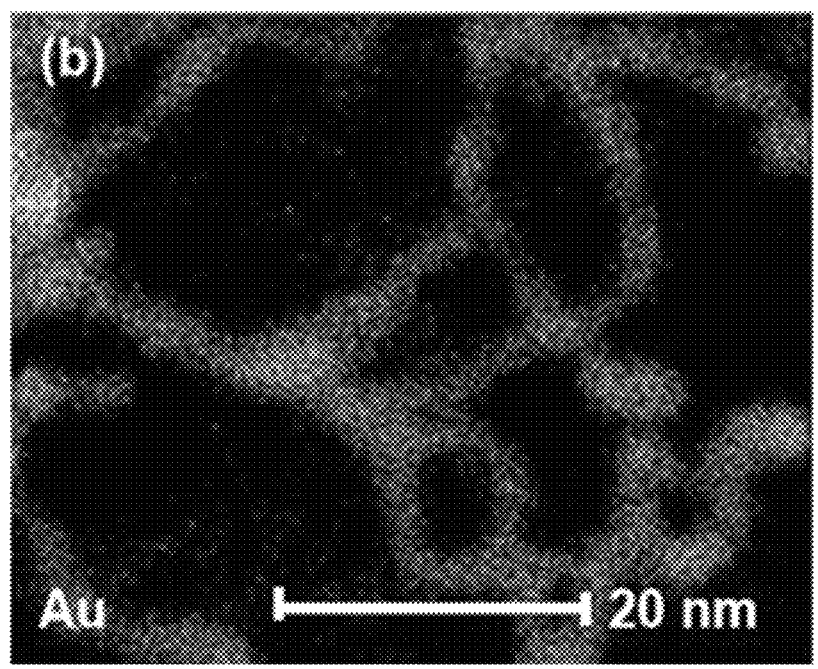
FIG. 11B is STEM-EDS mapping of Au in the dashed box of FIG. 12A.

Referring to FIG. 3A, powder X-ray diffraction (XRD) measurement showed that the nanowires were in alloy form with the primary (111) peak in between Au (111) and Cu (111) peaks. Referring to FIG. 1D and FIGS. 3B-3D, TEM characterization of the as-prepared nanowires showed the diameter of the nanowires was about 2-5 nm with uniform distribution of the Au and Cu along the nanowire. Referring to FIGS. 11A and 11B, the Au/Cu molar ratio was close to 1:1 as determined by energy dispersive X-ray spectrometry (EDS). Referring to FIGS. 2A-2C, the as-prepared nanowires contain polycrystalline grains that formed highly branched structures, which spontaneously formed a highly porous and mechanically robust network upon solvent removal.

Referring to FIGS. 11A and 11B, the membranes were wrinkled by hand to cause breakage of the membrane, aligning some pieces of the membrane vertically. SEM was then used to determine the thickness of the membrane. By varying the amount of AuCu nanowire deposited on the substrate and measuring the corresponding thickness, the porosity of the membrane was determined to be 40%. This high porosity can allow effective flow of reactants under very little applied pressure.

Example 2: Method of Using the Membrane

The cycloaddition of alkynes with azides to form 1, 2, 3 triazoles was carried out under ambient conditions using a flow chemistry process through a AuCu nanowire membrane. The AuCu nanowire membrane was made in accordance with Example 1 and contained 6.6 mg of nanowires. The reaction scheme is illustrated in FIG. 4.

In general, 0.25 mmol of alkyne (1 in the reaction scheme) and 0.5 mmol azide (2 in the reaction scheme) was mixed in 10 mL of ethanol. The solution was pumped through the AuCu nanowire membrane under vacuum with a flow rate of 5 mL/min. The products were detected by TLC. When the reaction was finished, the reaction product was washed with 5.0 mL ethanol three times and the solution was concentrated in vacuum. The pure product was obtained by flash column chromatography on silica gel (hexane/ethyl ether=10:1). The yield of product was determined by column chromatography.

A CuAAC reaction between phenylacetylene and benzyl azide was performed by flowing reactants through the nanoporus membrane under house vacuum (<1 bar) at room temperature. Various cycles were run changing one or more of the conditions from the standard reaction conditions, as illustrated in FIG. 5.

In each cycle of the standard reaction, 10 mL ethanol containing the reactants was circulated through the membrane ten times with a flow rate of 5 mL/min. It was found that the best results were obtained by performing the reaction in ethanol at room temperature. Replacing ethanol with water diminished the reaction yield slightly.

Figure 5:
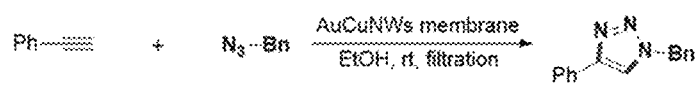
FIG. 5 is a table showing the results of CuAAC reaction between phenylacetylene and benzyl azide, with reactants flowing through the AuCu membrane under house vacuum (<1 bar) at room temperature in accordance with embodiments of the disclosure.

Nanowires with different compositions as outlined in entries 3-5 of FIG. 5 were tested based on prior reports that showed using scanning tunneling microscopy that click reaction can also occur on the Au (111) surface. It was found that in all Au-rich membranes, the catalysts were less effective. The yield of the reaction remained high when the copper content in the nanowire was beyond 50%.

It was further observed that replacing ambient conditions with Argon atmosphere resulted in reduced yield of only 30%. Without intending to be bound by theory, it is believed that air plays a role in the regeneration of the membrane for catalysis.

Figure 8:
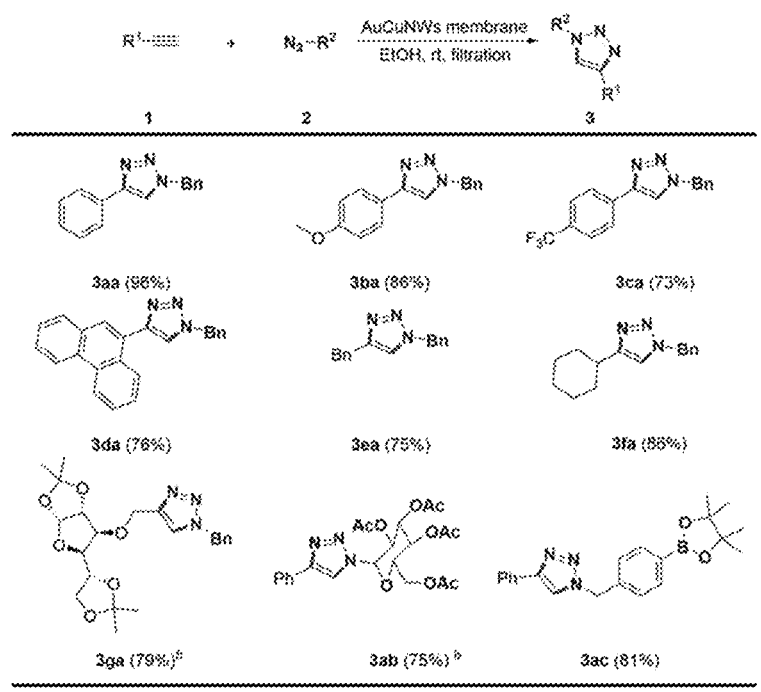
FIG. 8 is an illustration of the different reaction schemes and yields obtained with methods in accordance with embodiments of the disclosure.
Figure 9A:
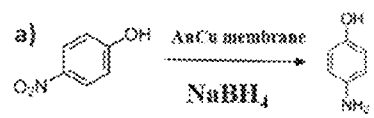
FIG. 9A is a schematic illustration of a reaction scheme and equipment set-up for performing reduction of 4-nitrophenol to 4-aminophenol catalyzed by AuCu nanowire membrane in accordance with embodiments of the disclosure.
Figure 9A:
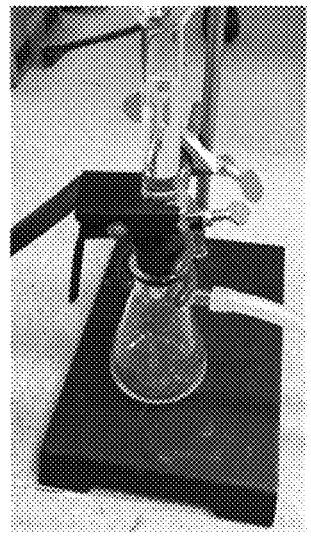
Figure 9B:
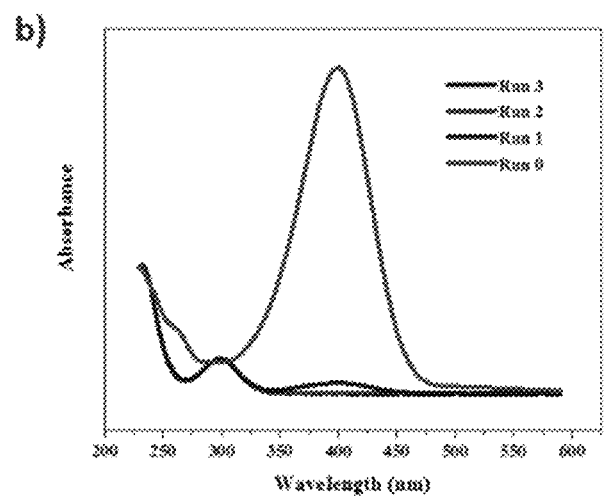
FIG. 9B is a graph of optical absorbance of the reactant (run 0) compared and the filtrate after passing through the membrane in consecutive (run 1, 2, 3) from the method illustrated in FIG. 9A.
Figure 9C:
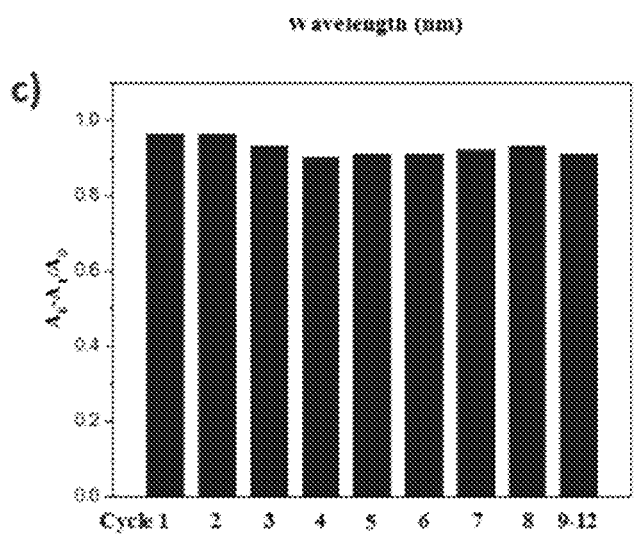
FIG. 9C is a graph showing yield of 4-aminophenol after repeated cycles of the method illustrated in FIG. 9A.
Figures 10A, 10B:
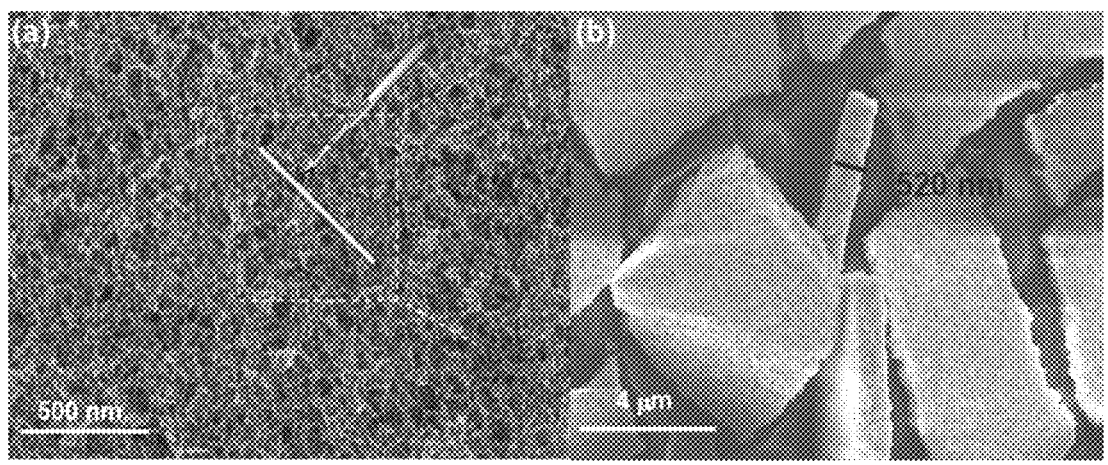
FIG. 10A is an SEM image of a top surface of an AuCu membrane in accordance with embodiments of the disclosure.
FIG. 10B is a SEM image of the membrane cross-section of FIG. 11 after being wrinkled.

The flow chemistry based catalytic reaction was extended to CuAAC reactions with other types of alkynes and azides as illustrated in FIG. 8. The reaction time was 12 hours.

Adding electron-donating or electron-withdrawing substituents to the phenyl group in the alkyne did not significantly affect yield in the CuAAC reaction. Other types of alkynes, including 9-ethynylphenanthrene, 3-phenyl-1-propyne, and cyclohexylacetylenes also worked well. Dioxaborolane modified azide was found to react effective with phenylacetylene through the membrane, Detailed nuclear magnetic resonance spectroscopy NMR of the reaction products was shown in FIGS. 14-22.

Several important pharmaceutical drugs, such as α-glucosidase inhibitors, can be synthesized using this strategy with relatively good yield, as shown by triazolyl glycoconjugates (3ga-3ab).

Example 3: Scale-Up Analysis

The flow chemistry process used in Example 2 was found to scale easily to produce reaction product on the gram scale. The model reaction illustrated in FIG. 5 was scaled up by continuously flowing the reactants through the membrane overnight, resulting in 1.81 g of reaction product in 77% yield with a turnover number of 5133.

Example 4: Reusability Study

Figure 11C:
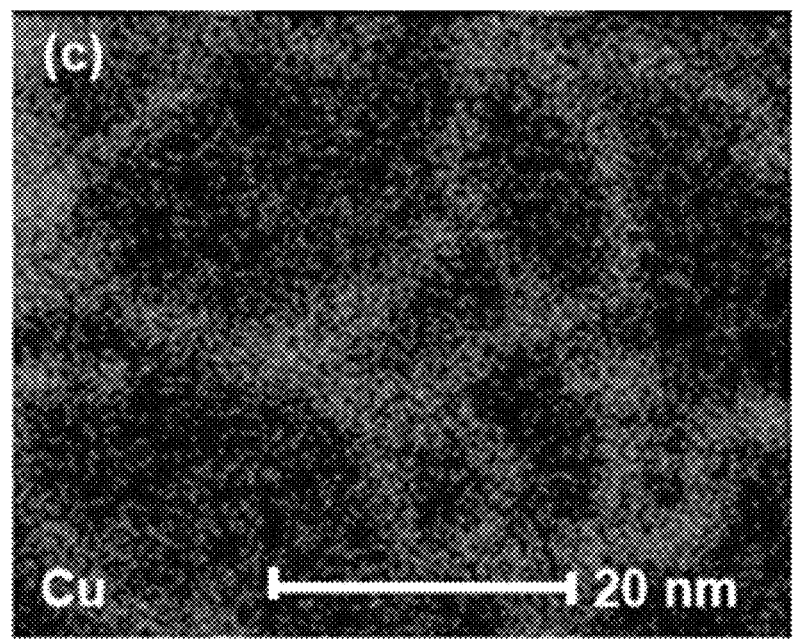
FIG. 11C is an STEM-EDS mapping of Cu in the dashed box of FIG. 12A.

The reusability of the catalysts was analyzed by repeating cycles using the same membrane under the standard reaction conditions described in Example 2, but with a new batch of reactants during each cycle. Referring to FIG. 6a, it was found that there is a slight but visible decrease in activity to 89% after five cycles, but that the overall activity remained relatively high. Referring to FIG. 11, STEM image of the membrane after five cycles showed no visible change in the structure of the membrane. As shown in Table 1 below, inductive coupled plasma mass spectrometry (ICP-MS) results of the reaction mixture after five cycles indicated that only a small amount of Cu (7.8 ppm, 3% of Cu in the membrane) was present in the product. This is significantly lower than the 15 ppm permitted in the pharmaceutical industry. No gold was detected by ICP-MS (<0.07 ppm).

| Analysis | Method | Sample Amount Used | Results |
| --- | --- | --- | --- |
| Au | GLI procedure ME-30* | 2515.21 mg | 0.069 ppm |
| Cu | GLI procedure ME-30* | 2515.21 mg | 7.8 ppm |

*Independent analysis was performed by Galbraith Inc., Knoxville, TN USA according to their protocol.

The results show that the AuCu membrane is highly stable under this reaction condition. Referring to FIG. 6B, to investigate whether the leached Cu was driving the reaction in solution directly, the reaction was slowed down by allowing the reactants to drip through the membrane directly without vacuum. The yield of the product was monitored by $^1$H nuclear magnetic resonance ($^1$H NMR). After 1 hour, the reaction was stopped and the bottom filtrate was stirred without making contact with the membrane for the next 3 hours. During this stoppage time, there was no increase of product yield, which indicated that the leached Cu ions do not play a role in promoting the reaction. Only after the filtrate was recirculated through the membrane did the reaction yield start to increase again. This indicated that the CuAAC reaction occurred at the AuCu nanowire surface.

The AuCu nanowire membrane was examined before and after the reaction by X-ray photoelectron spectroscopy (XPS). XPS data were collected using the AXIS Nova spectrometer (Kratos Analytical) equipped with a monochromatic Al Kα X-ray source. The Al anode was powered at 10 mA and 15 kV. Instrument base pressure was ca. $1 \times 10^{-10}$ Torr. The analysis area size was $0.3 \times 0.7$ mm$^2$. For calibration purposes, the binding energies were referenced to C 1s peak at 284.4 eV, which also provided the binding energy of Au $4f_{7/2}$ peak at 84.0 eV. Survey spectra were collected with a pass energy of 20 eV and 0.1 eV step size. XPS peaks were fitted with an asymmetric Gaussian/Lorentzian peak shape (GL30) with Shirley background correction.

The AuCu membrane and the membrane after five cycles of CuAAC reaction were protected under Argon prior to the XPS experiment in order to maintain their native chemical state. Referring to FIG. 7A, the XPS survey data revealed two differences before and after the reaction: (1) there was a clear reduction of O 1s peak intensity relative to Cu 2p and Au 4f peak after the CuAAC reaction; and (2) the surface of the AuCu nanowires after the reaction presented a N 1s signal, which is believed to be the result of absorption of reaction product 1, 2,3-triazole. Referring to FIG. 7B, detailed studies in the C 1s region showed that the peak associated with C—O (286.21 eV) decreased significantly after the reaction, and the peak associated with sp$^2$ C—C (284.69 eV) remained the same. Although a thorough post synthesis washing step was performed to remove weakly bound surfactant Triton X-100, some surfactant remained attached to the nanowire surface. The strong C—O peak was from the remaining Triton X-100. Once they were replaced by the CuAAC reaction substrates, which have higher affinity for the nanowire surface, the C—O peak greatly diminished. Several new peaks also emerged after the reaction, all of which can be attributed reactants or products, with 282.15 eV corresponding to carbon incorporated into the alloy to form a structure very similar to metal carbide. The signals at 285.31, 286.20, and 291.10 eV were assigned to the c-N, sp$^3$ C—C, and π-π*, respectively.

Figures 12A, 12B:
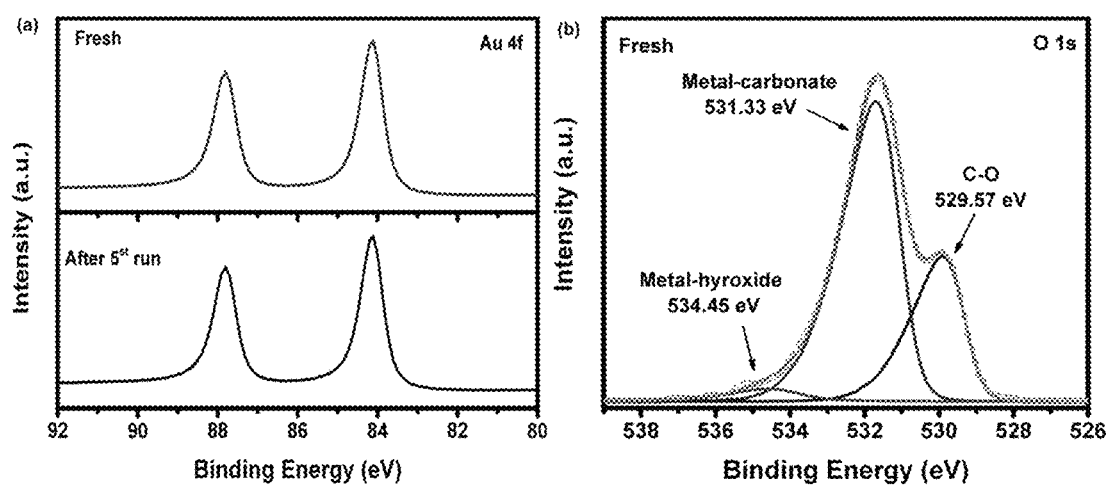
FIG. 12A is a high-resolution XPS spectra of Au 4f in AuCu nanowires in accordance with the disclosure.
FIG. 12B is a high-resolution XPS spectra of O 1s in AuCu nanowires in accordance with the disclosure.
Figure 13A:
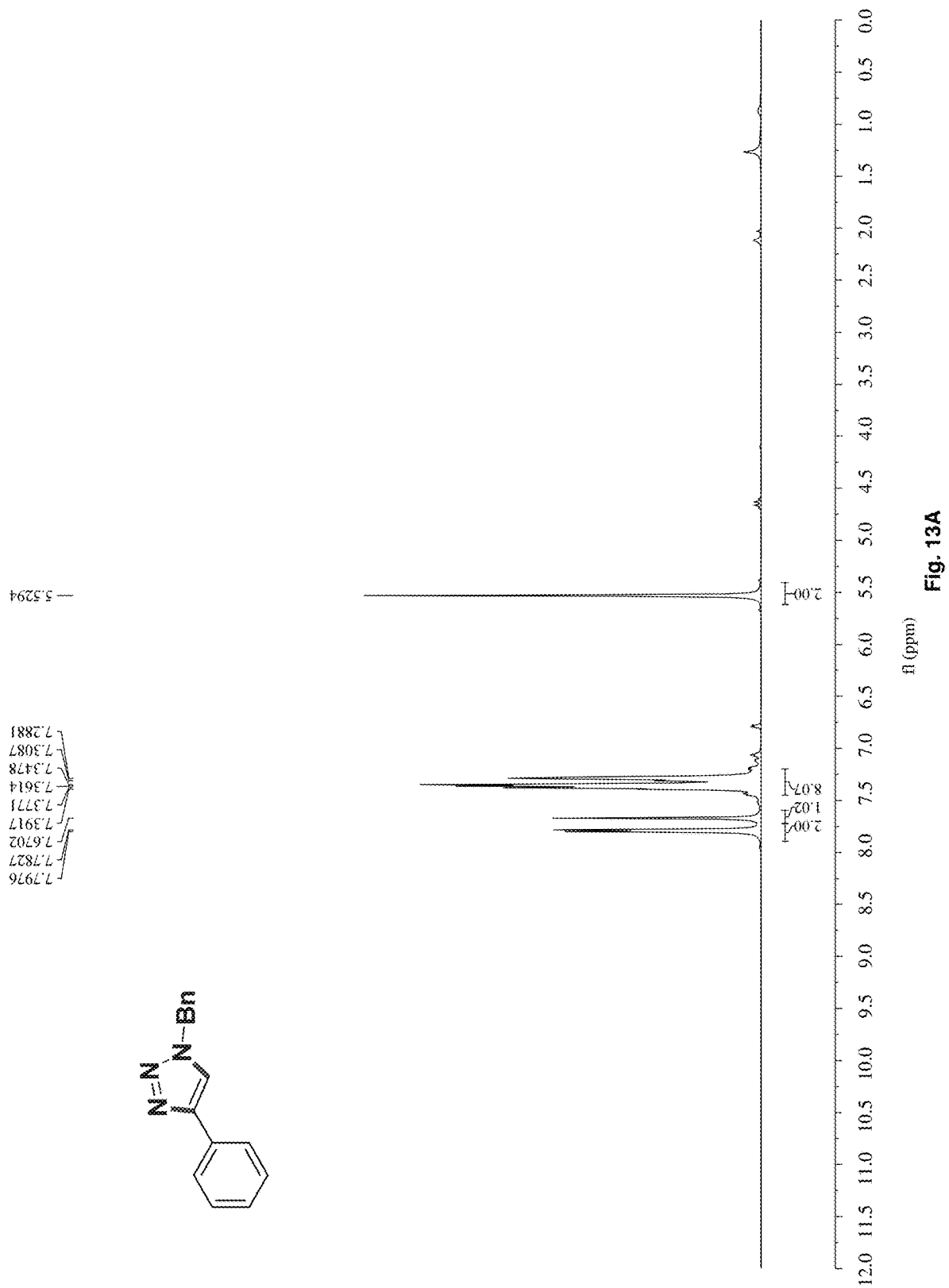
FIG. 13A is a $^1H$ NMR spectra of 1-benzyl-4-phenyl-1H-1,2,3-triazole made by a method in accordance with embodiments of the disclosure.
Figure 13B:
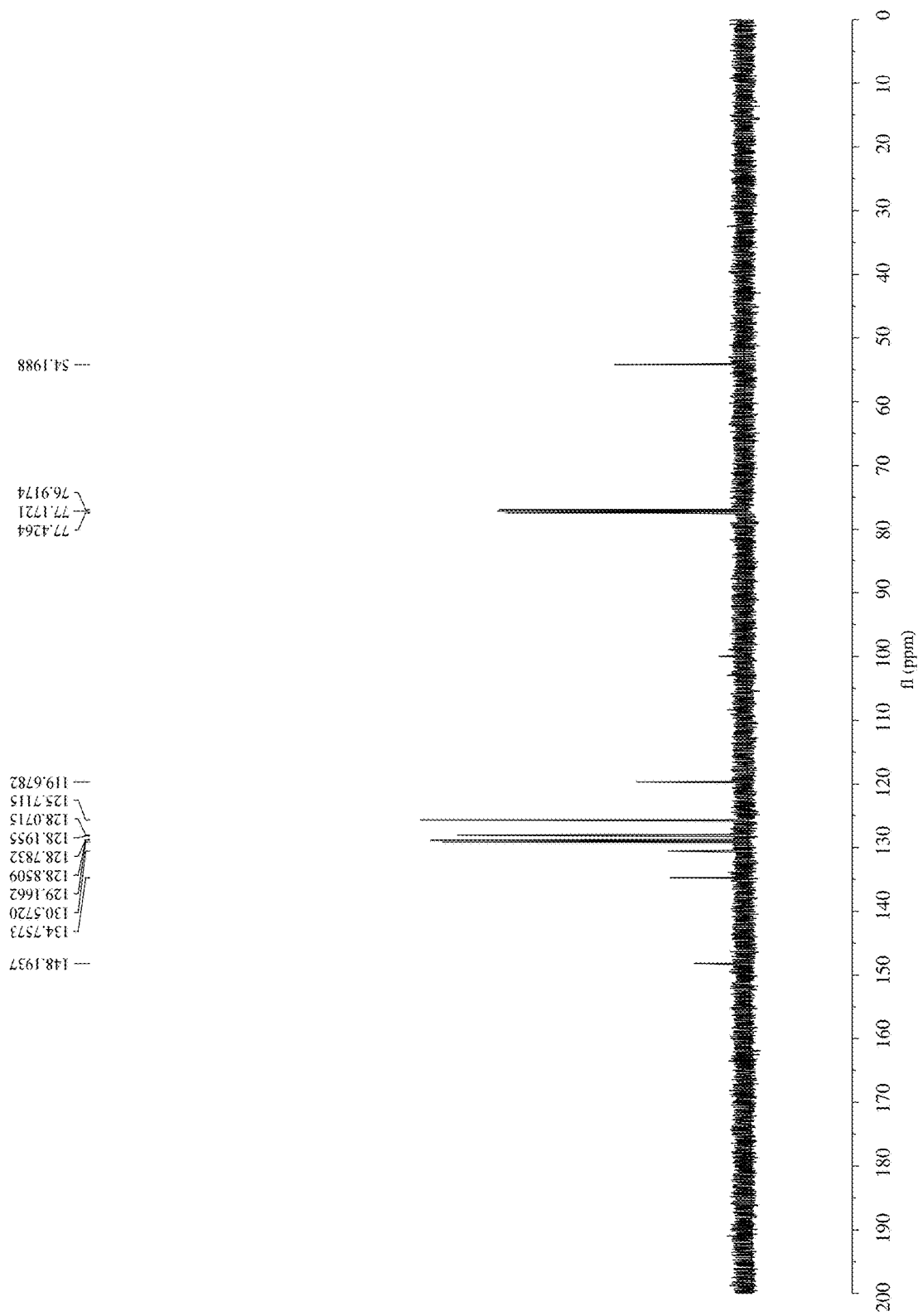
FIG. 13B is $^{13}C$ NMR spectra of the 1-benzyl-4-phenyl-1H-1,2,3-triazole of FIG. 13A.
Figure 14A:
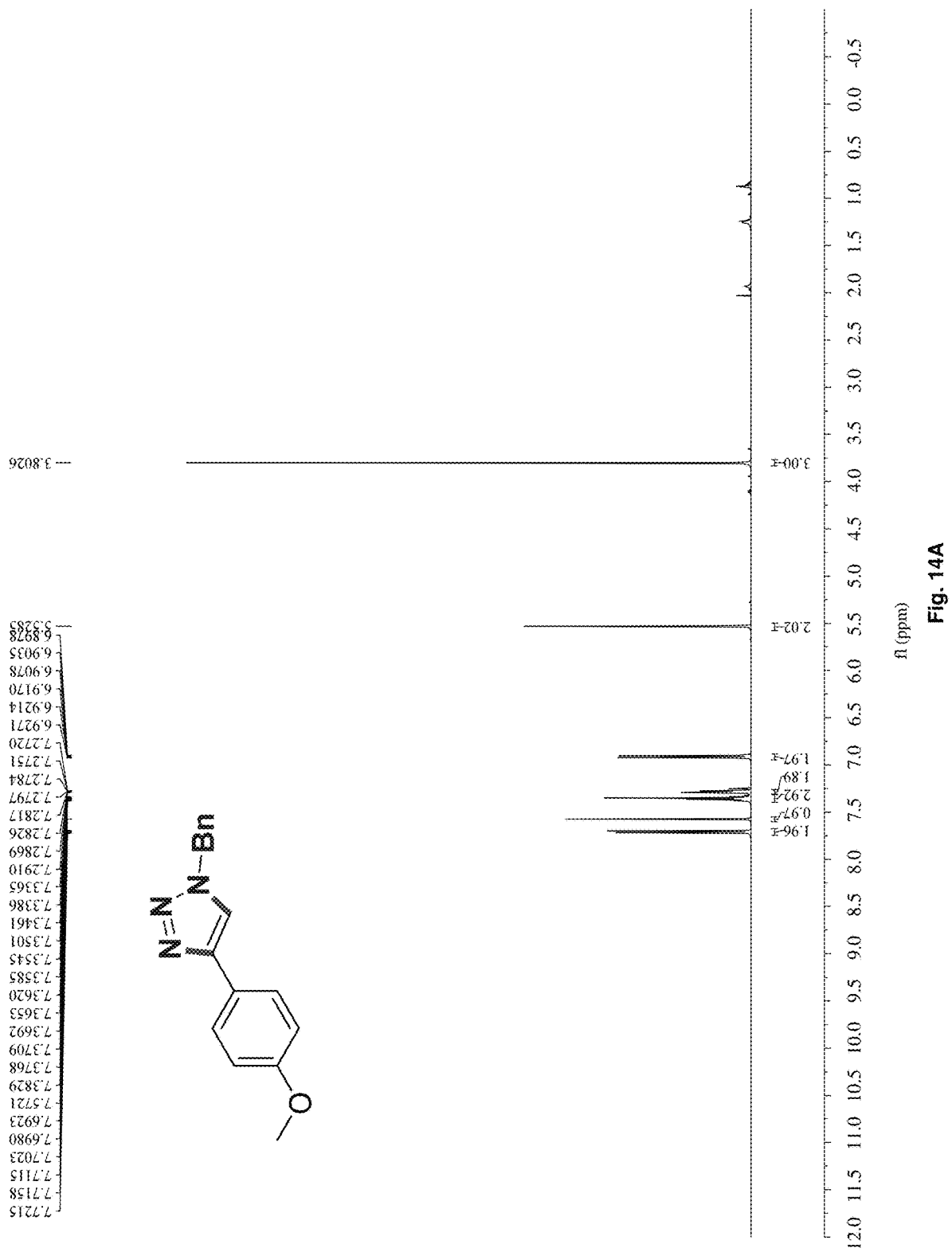
FIG. 14A is a $^1H$ NMR spectra of 1-benzyl-4-(4-methoxyphenyl)-1H-1,2,3-triazole made by a method in accordance with embodiments of the disclosure.
Figure 14B:
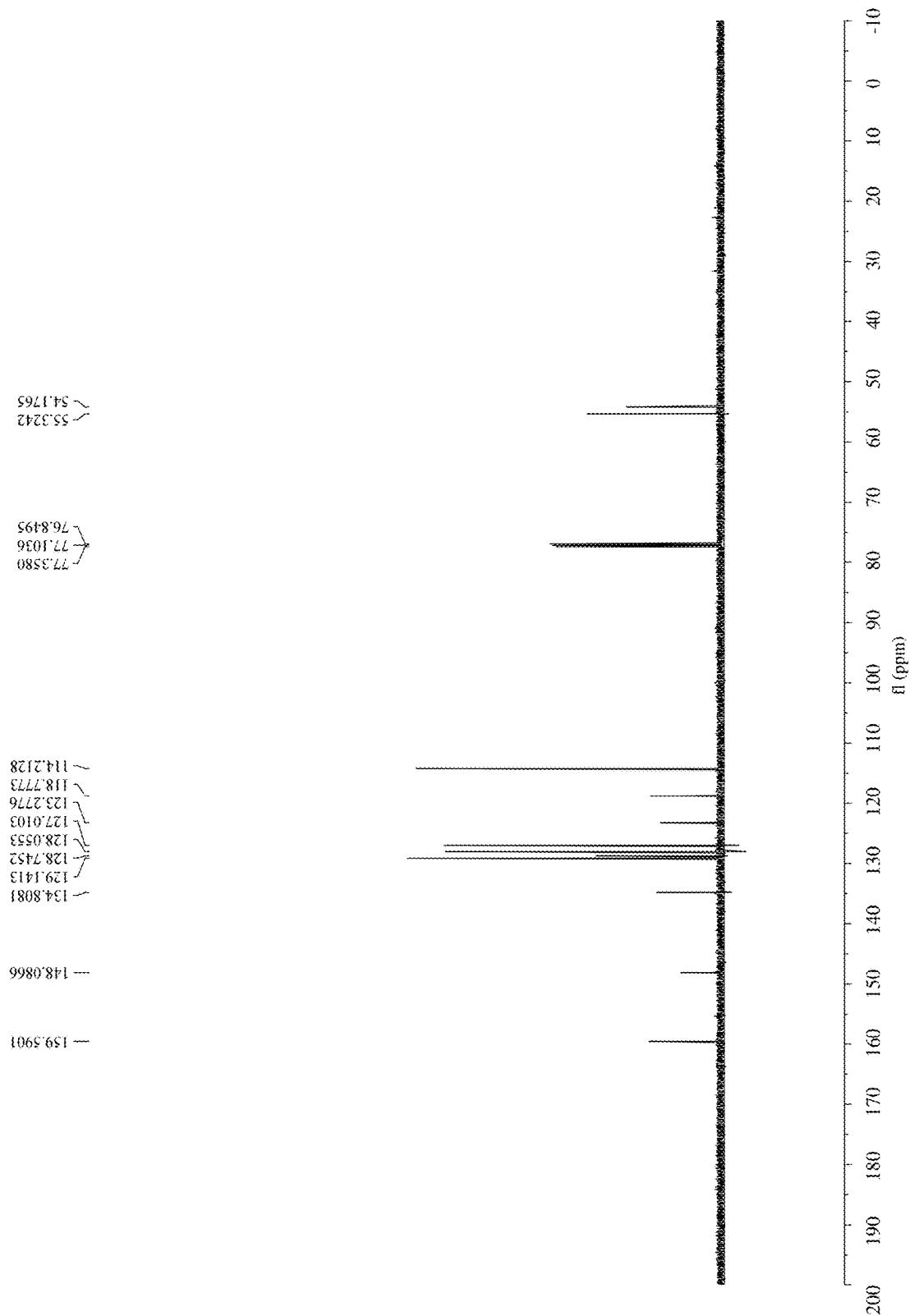
FIG. 14B is $^{13}C$ NMR spectra of the 1-benzyl-4-(4-methoxyphenyl)-1H-1,2,3-triazole of FIG. 14A.
Figure 15A:
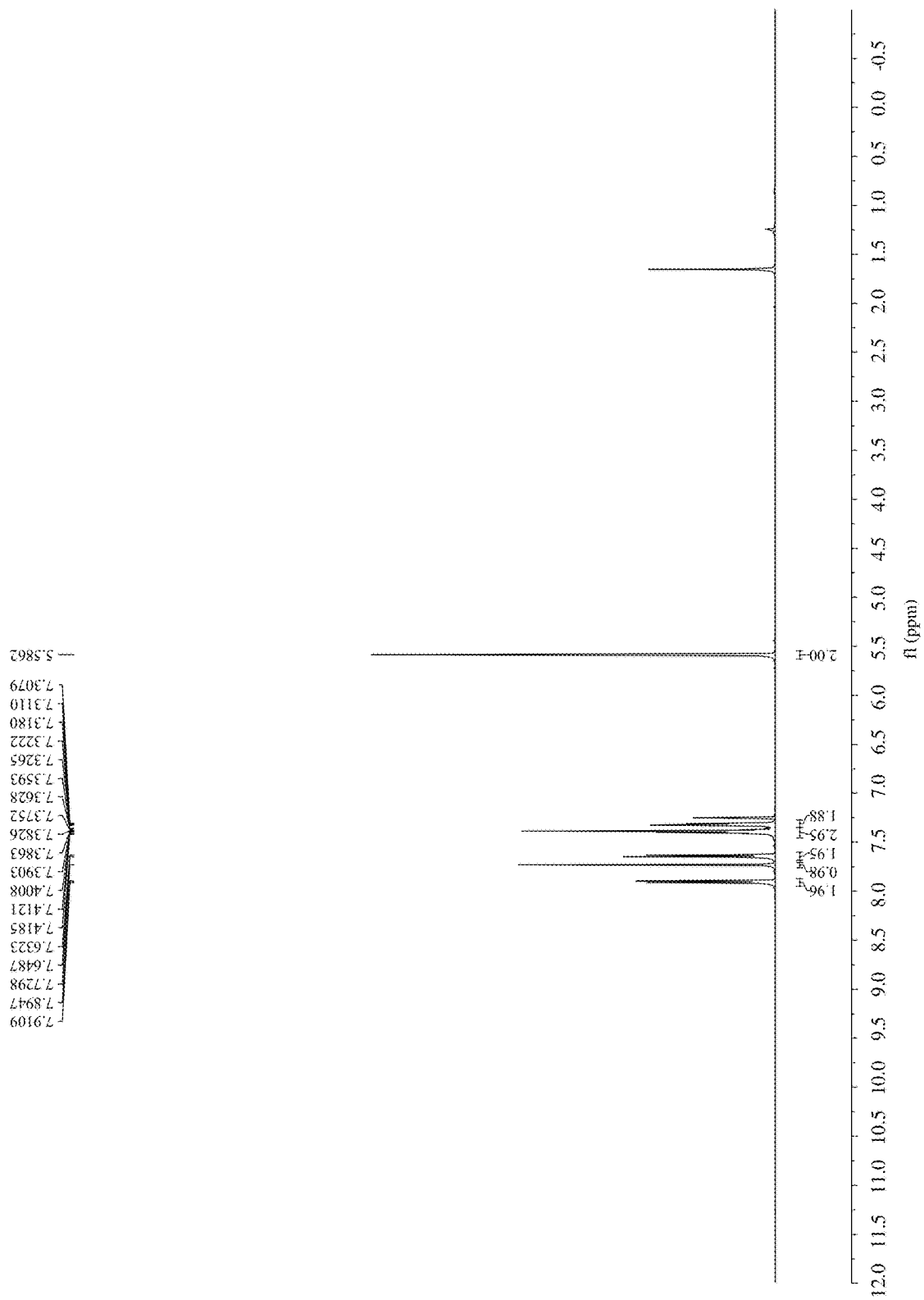
FIG. 15A is a $^1H$ NMR spectra of 1-benzyl-4-(4-trifluoromethyl)phenyl)-1H-1,2,3-triazole made by a method in accordance with embodiments of the disclosure.
Figure 15B:
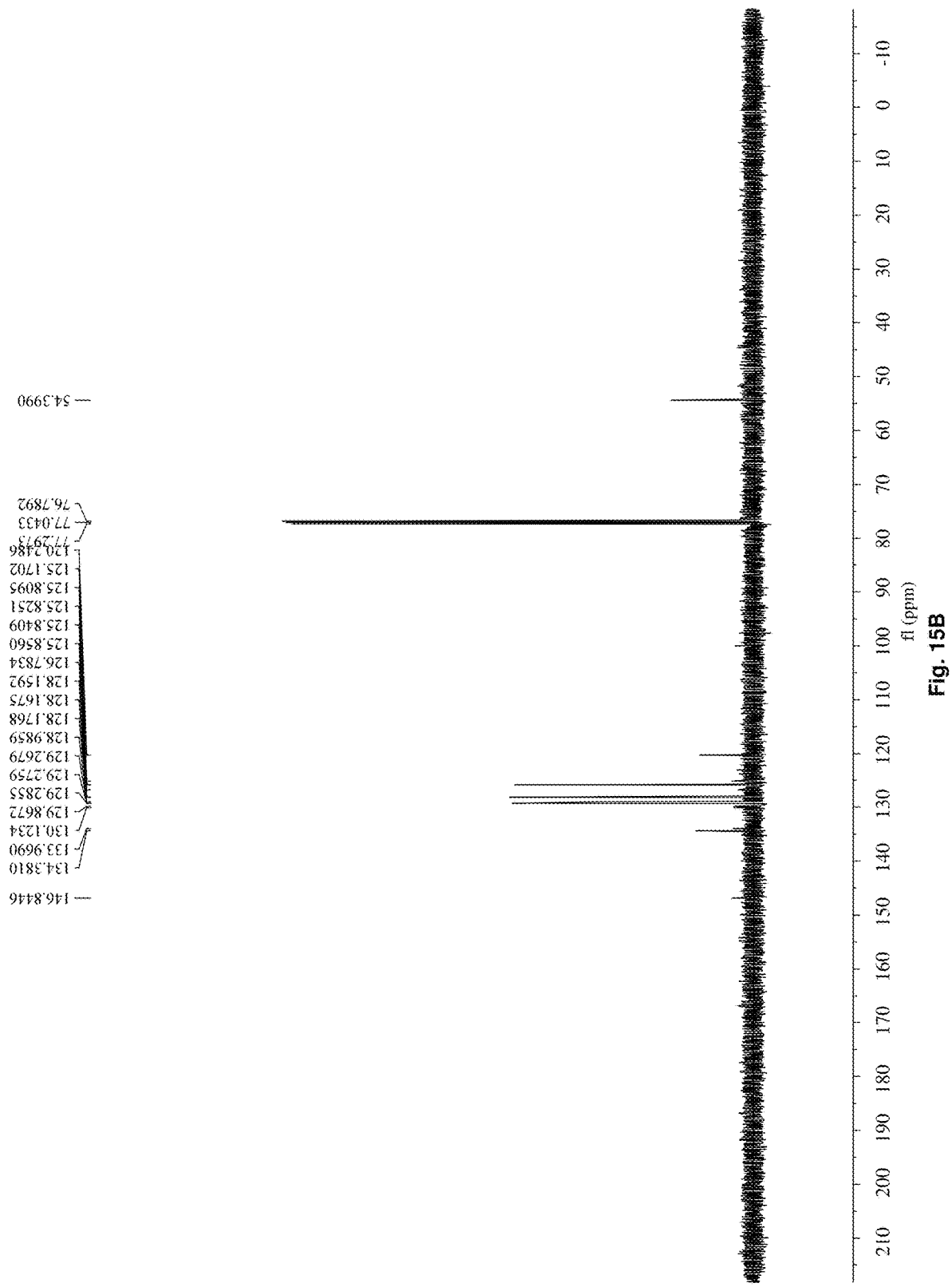
FIG. 15B is $^{13}C$ NMR spectra of the 1-benzyl-4-(4-trifluoromethyl)phenyl)-1H-1,2,3-triazole of FIG. 15A.
Figure 15C:
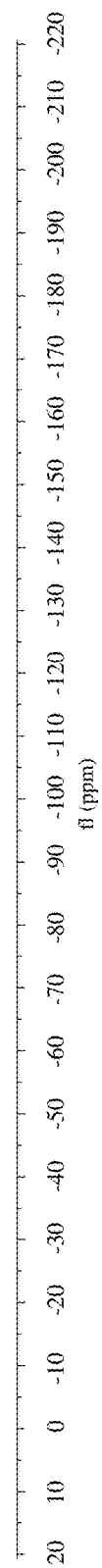
FIG. 15C is $^{19}F$ NMR spectra of the 1-benzyl-4-(4-trifluoromethyl)phenyl)-1H-1,2,3-triazole of FIG. 15A
Figure 16A:
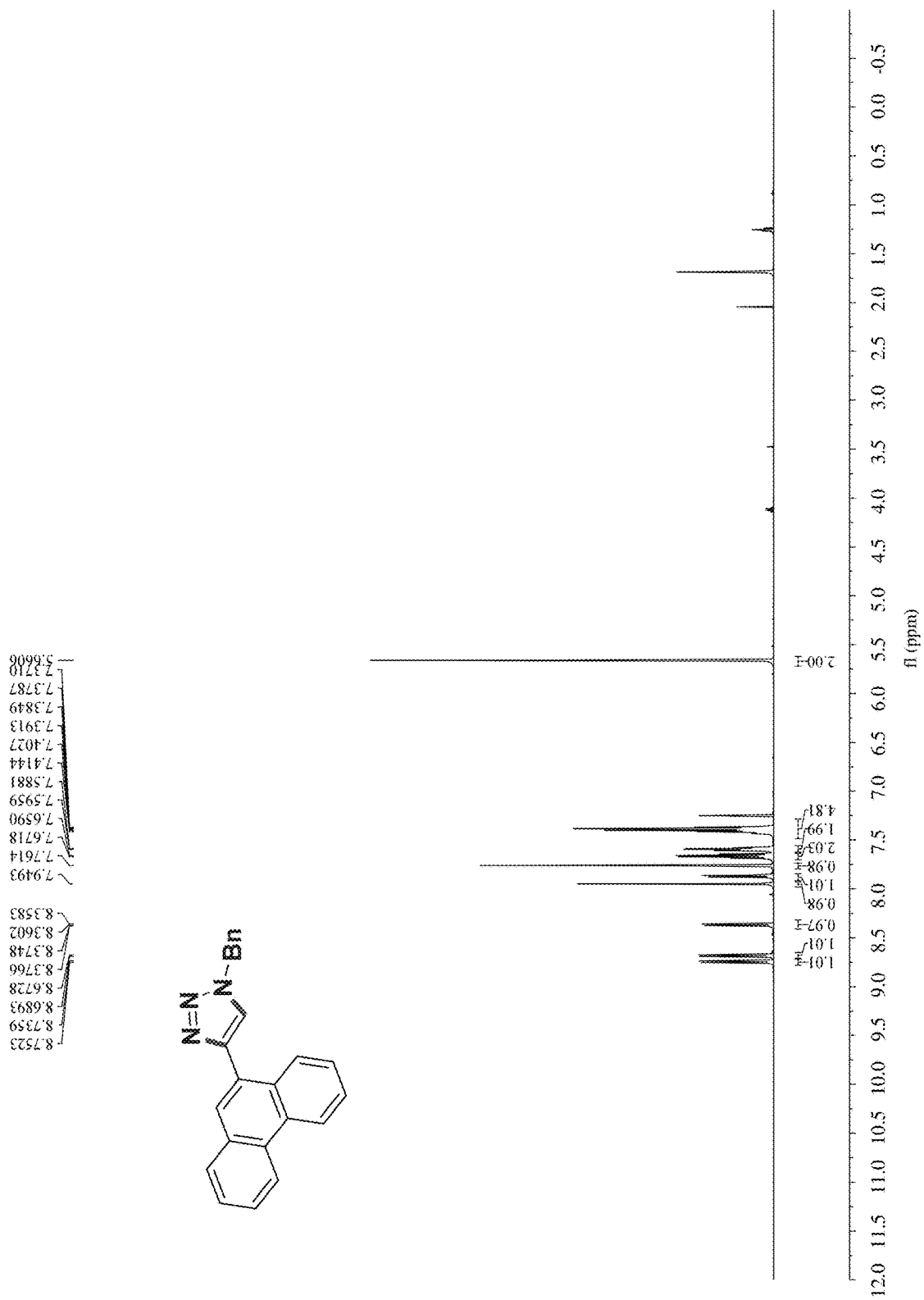
FIG. 16A is a $^1H$ NMR spectra of 1-benzyl-4-(phenanthrene-9-yl)-1H-1,2,3-triazole made by a method in accordance with embodiments of the disclosure.
Figure 16B:
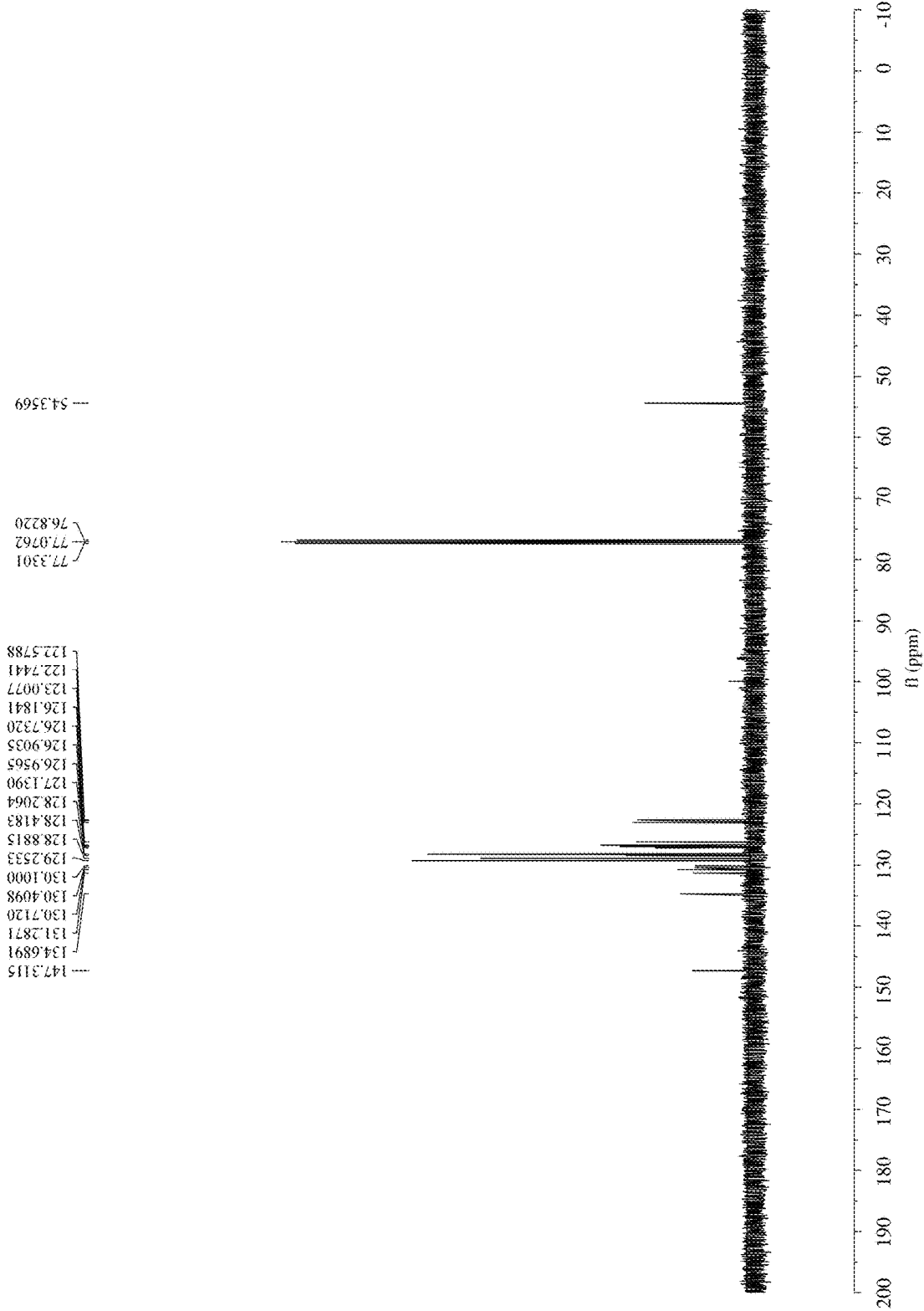
FIG. 16B is $^{13}C$ NMR spectra of the 1-benzyl-4-(phenanthrene-9-yl)-1H-1,2,3-triazole of FIG. 16A.
Figure 17A:
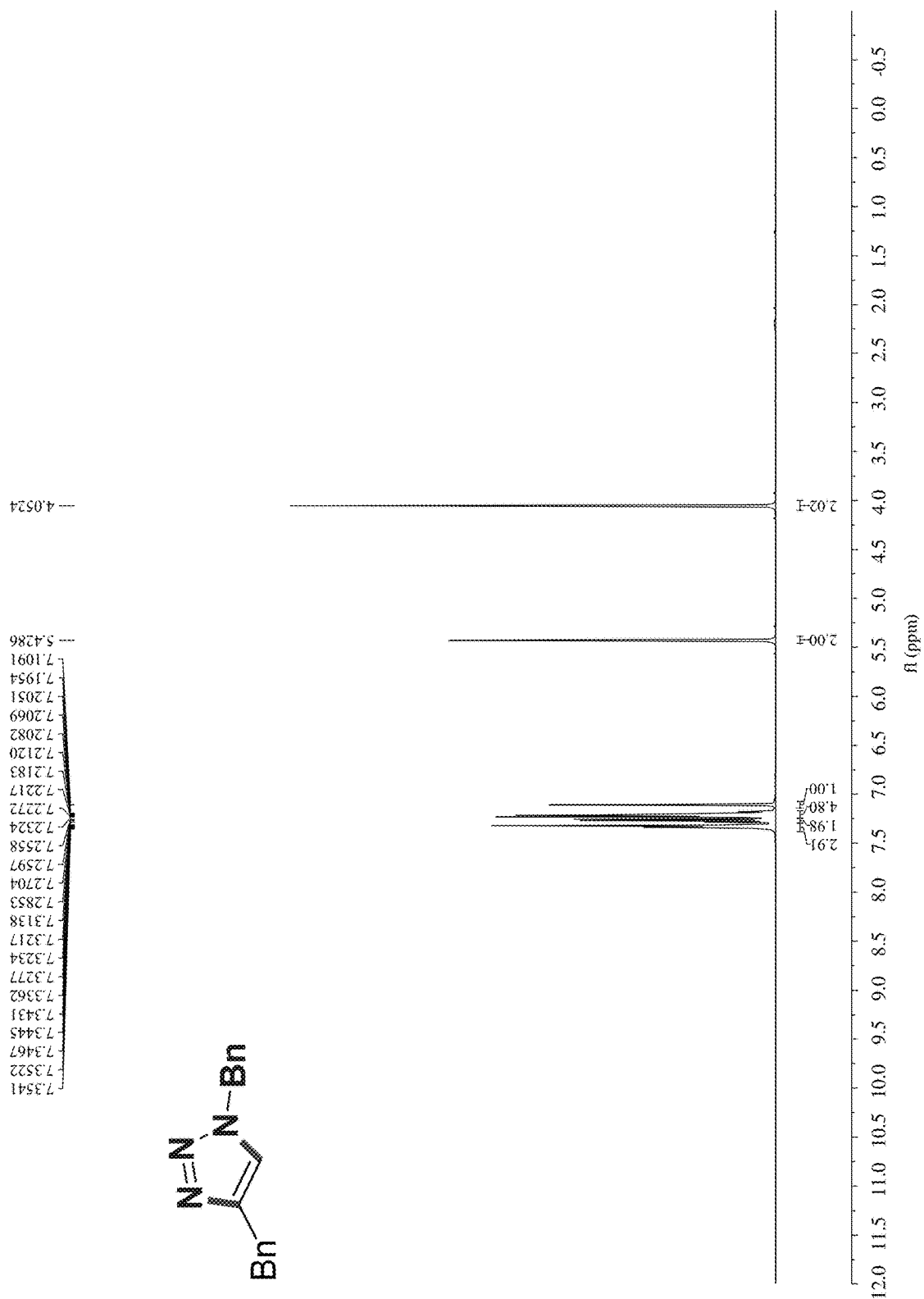
FIG. 17A is a $^1H$ NMR spectra of 1,4-dibenzyl-1H-1,2,3-triazole made by a method in accordance with embodiments of the disclosure.
Figure 17B:
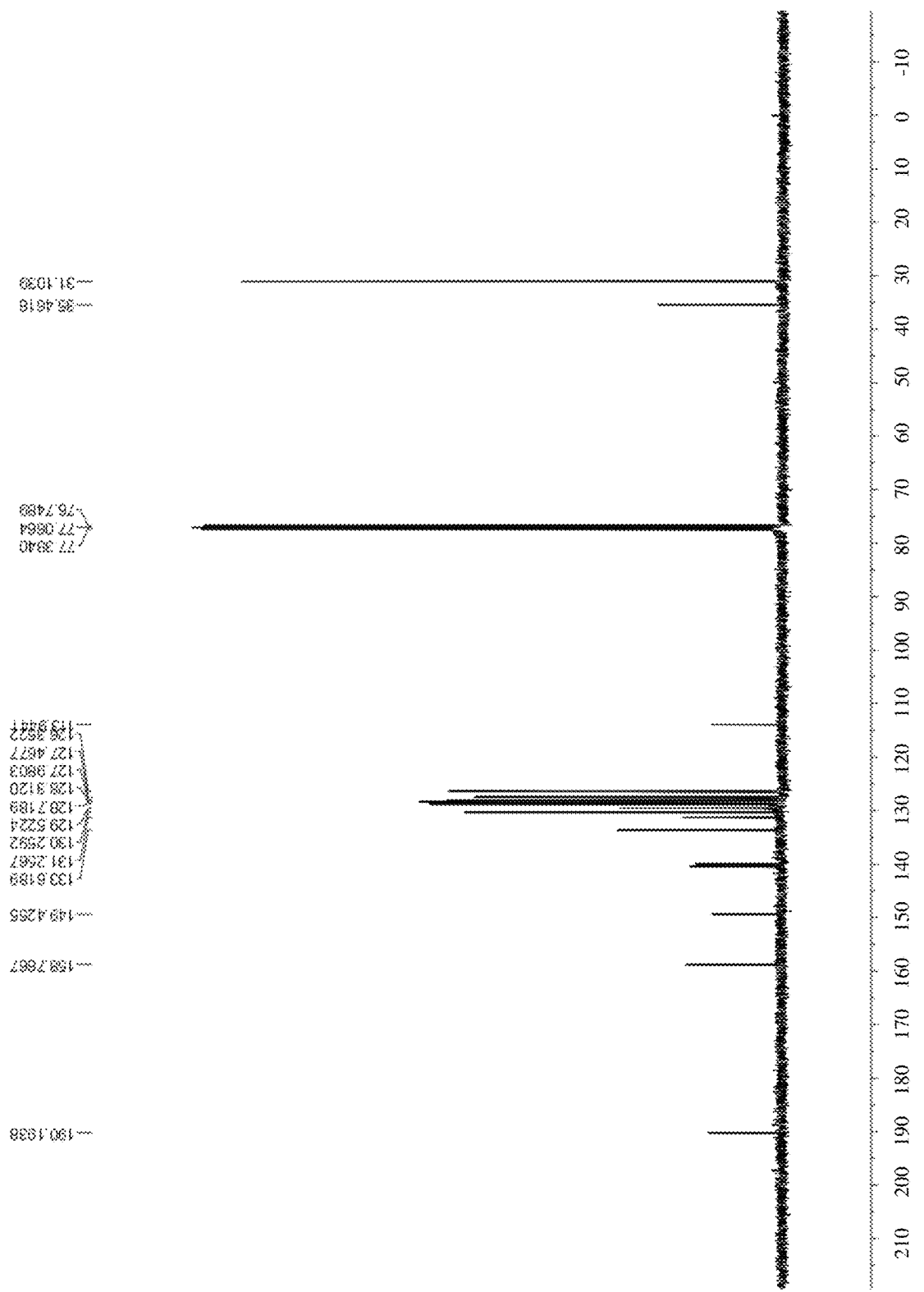
FIG. 17B is $^{13}C$ NMR spectra of the 1,4-dibenzyl-1H-1,2,3-triazole of FIG. 17A.
Figure 18A:
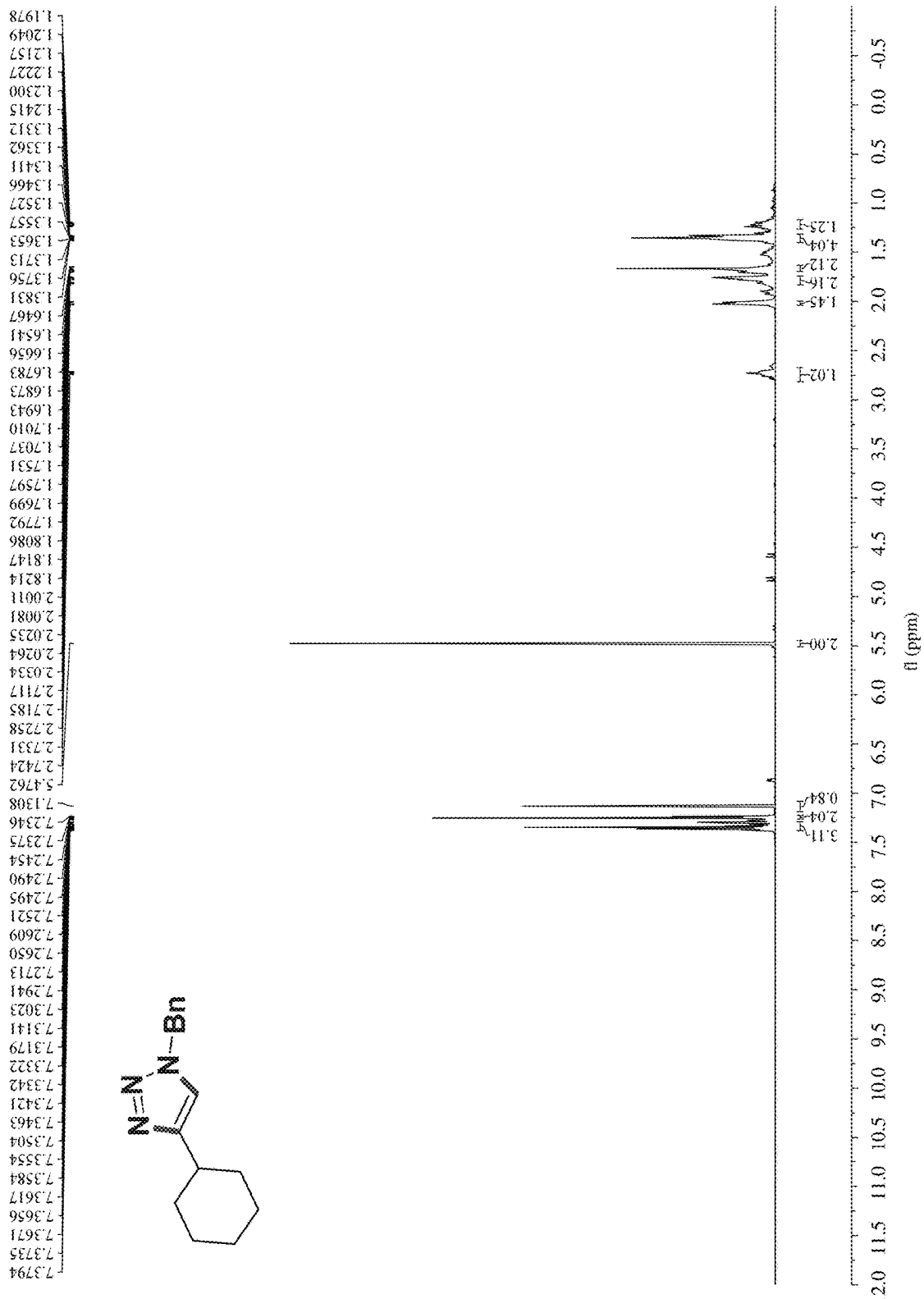
FIG. 18A is a $^1H$ NMR spectra of 1-benzyl-4-cyclohexyl-1H-1,2,3-triazole made by a method in accordance with embodiments of the disclosure.
Figure 18B:
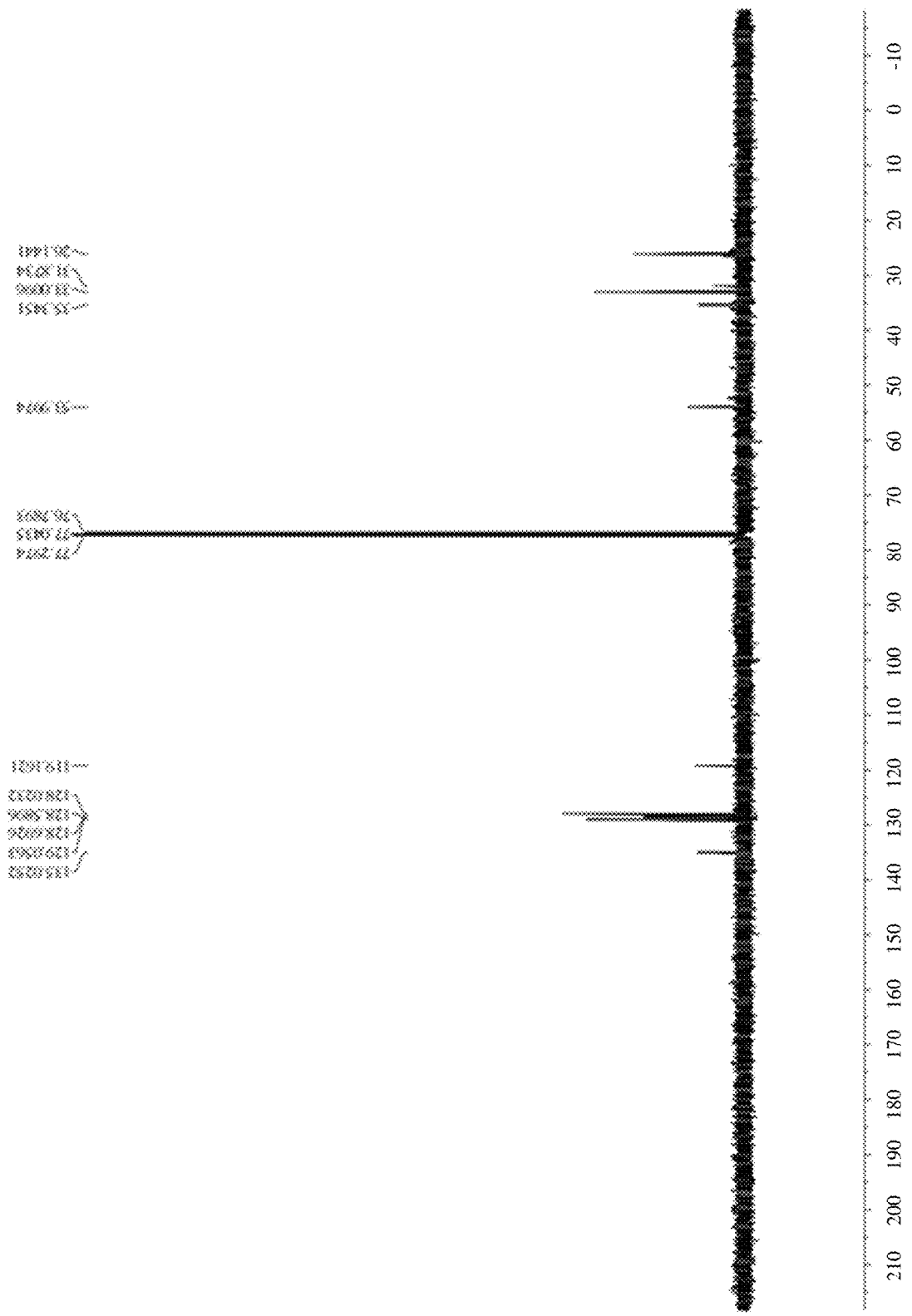
FIG. 18B is $^{13}C$ NMR spectra of the 1-benzyl-4-cyclohexyl-1H-1,2,3-triazole of FIG. 18A.
Figure 19A:
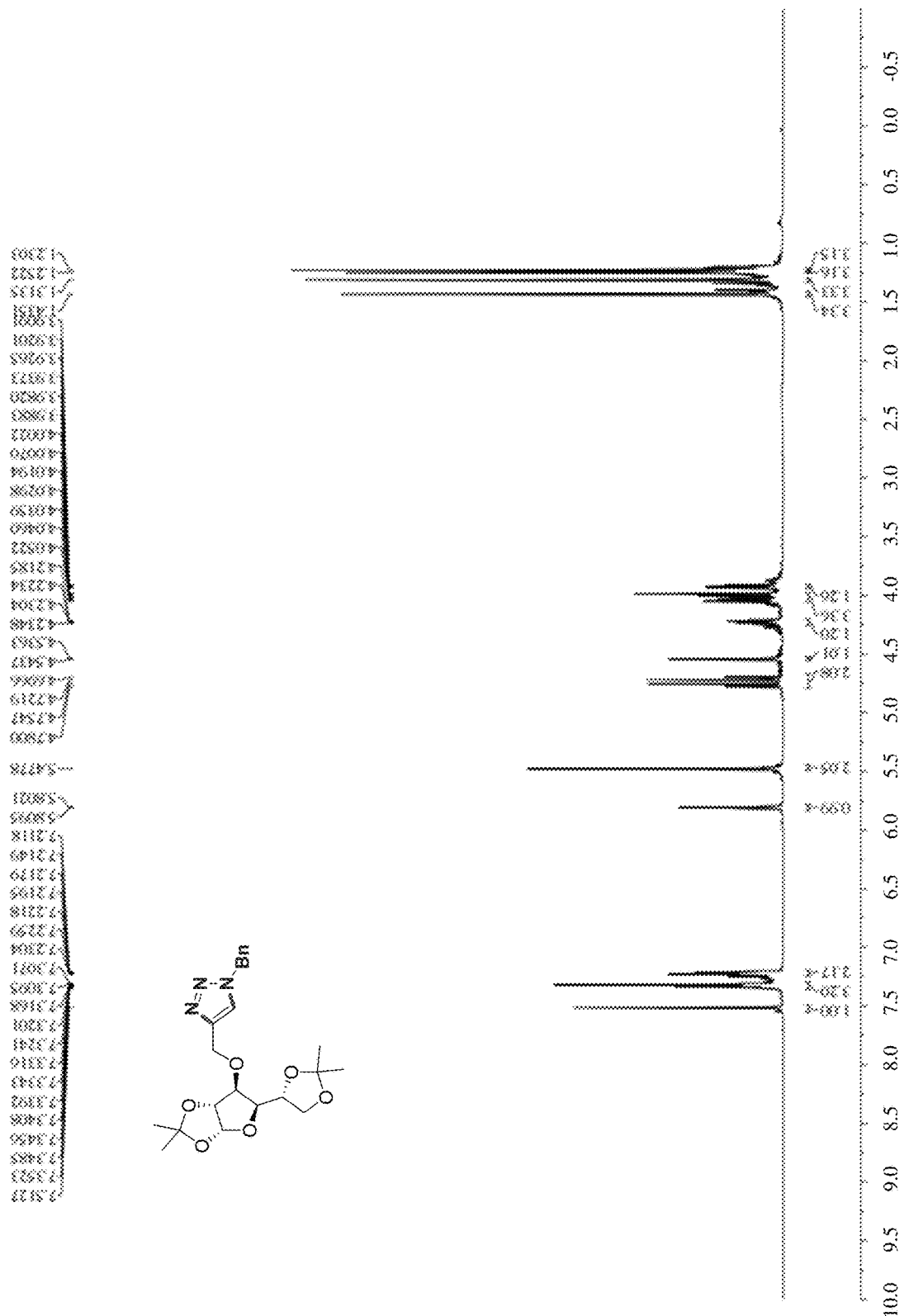
FIG. 19A is a $^1H$ NMR spectra of 1-benzyl-4-((((3aR,5R,6S,6aR)-5-((R)-2,2-dimethyl-1,3-dixolan-4-yl)-2,2-dimethyltetrahydrofuro[2,3,-d][1,3]dioxol-6-yl)oxy)methyl)-1H-1, 2,3-triazole made by a method in accordance with embodiments of the disclosure.
Figure 19B:
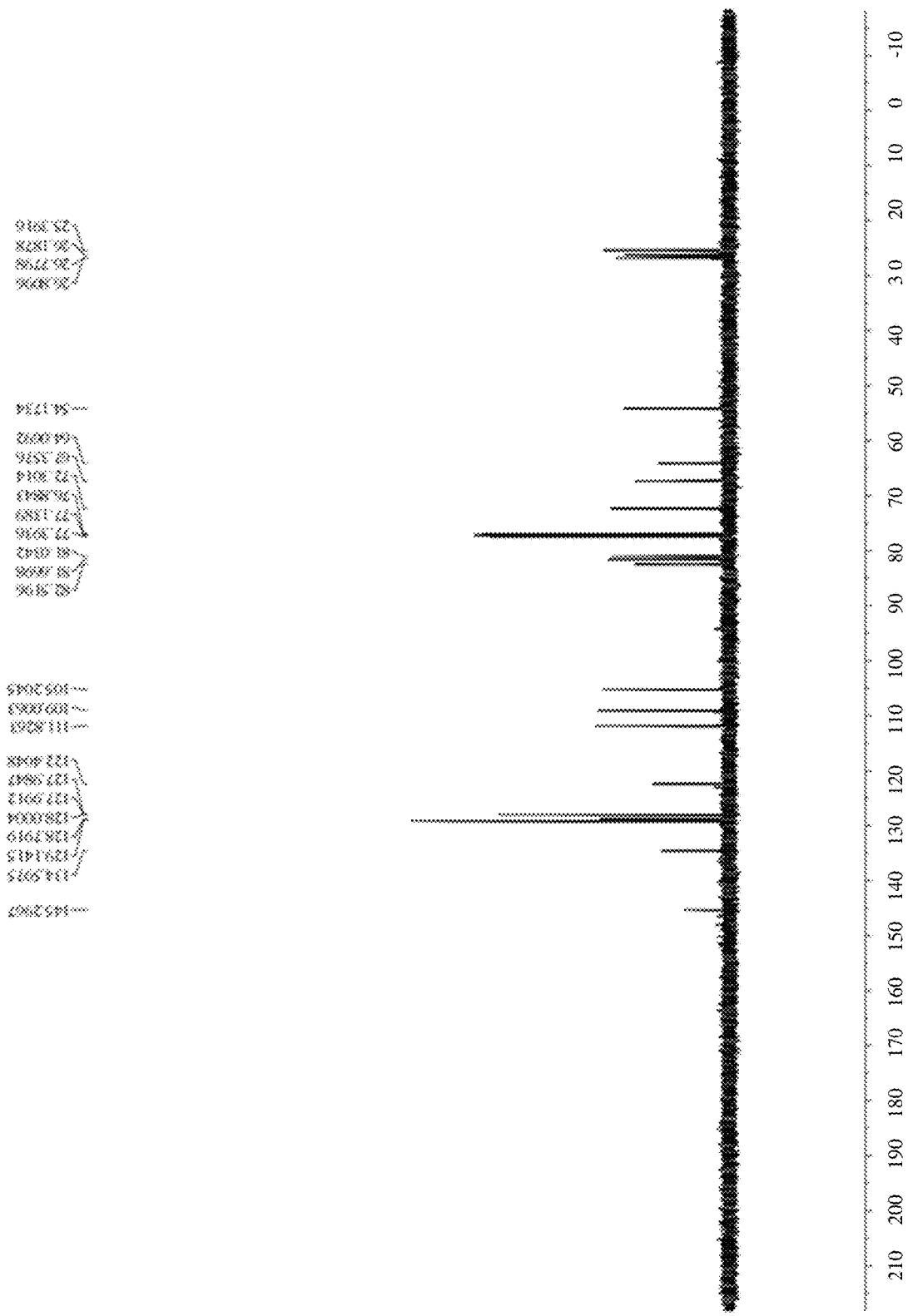
FIG. 19B is $^{13}$C NMR spectra of the 1-benzyl-4-(((((3aR, 5R,6S,6aR)-5-((R)-2,2-dimethyl-1,3-dixolan-4-yl)-2,2-dimethyltetrahydrofuro[2,3,-d][1,3]dioxol-6-yl)oxy)methyl)-1H-1,2,3-triazole of FIG. 19A.
Figure 20A:
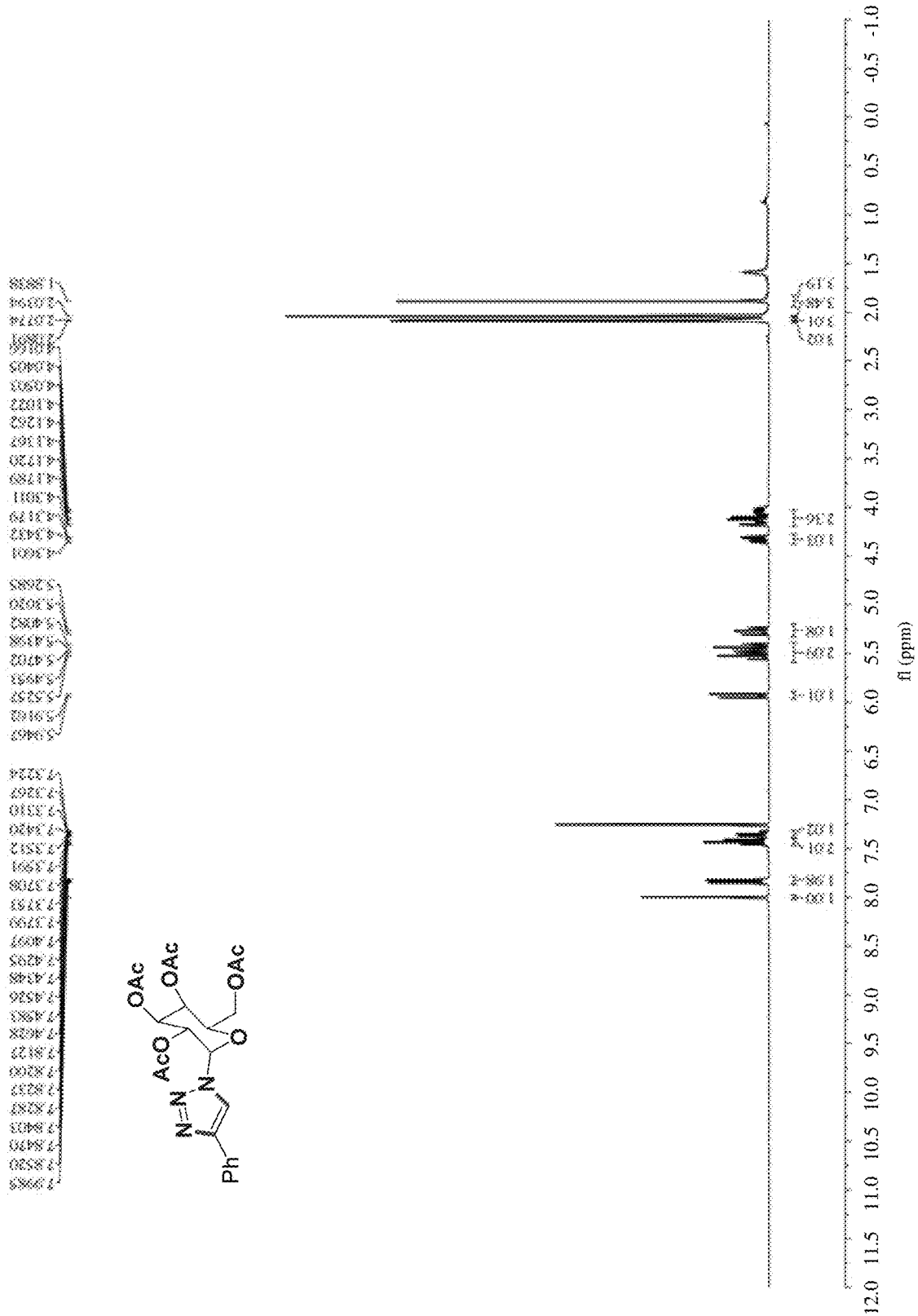
FIG. 20A is a $^1$H NMR spectra of (2S,3R,4R,5S,6R)-2-(acetoxymethyl)-6-(4-phenyl-1H-1,2,3-triazol-1-yl)tetrahydro-2H-pyran-3,4,5-triyl triacetate made by a method in accordance with embodiments of the disclosure.
Figure 20B:
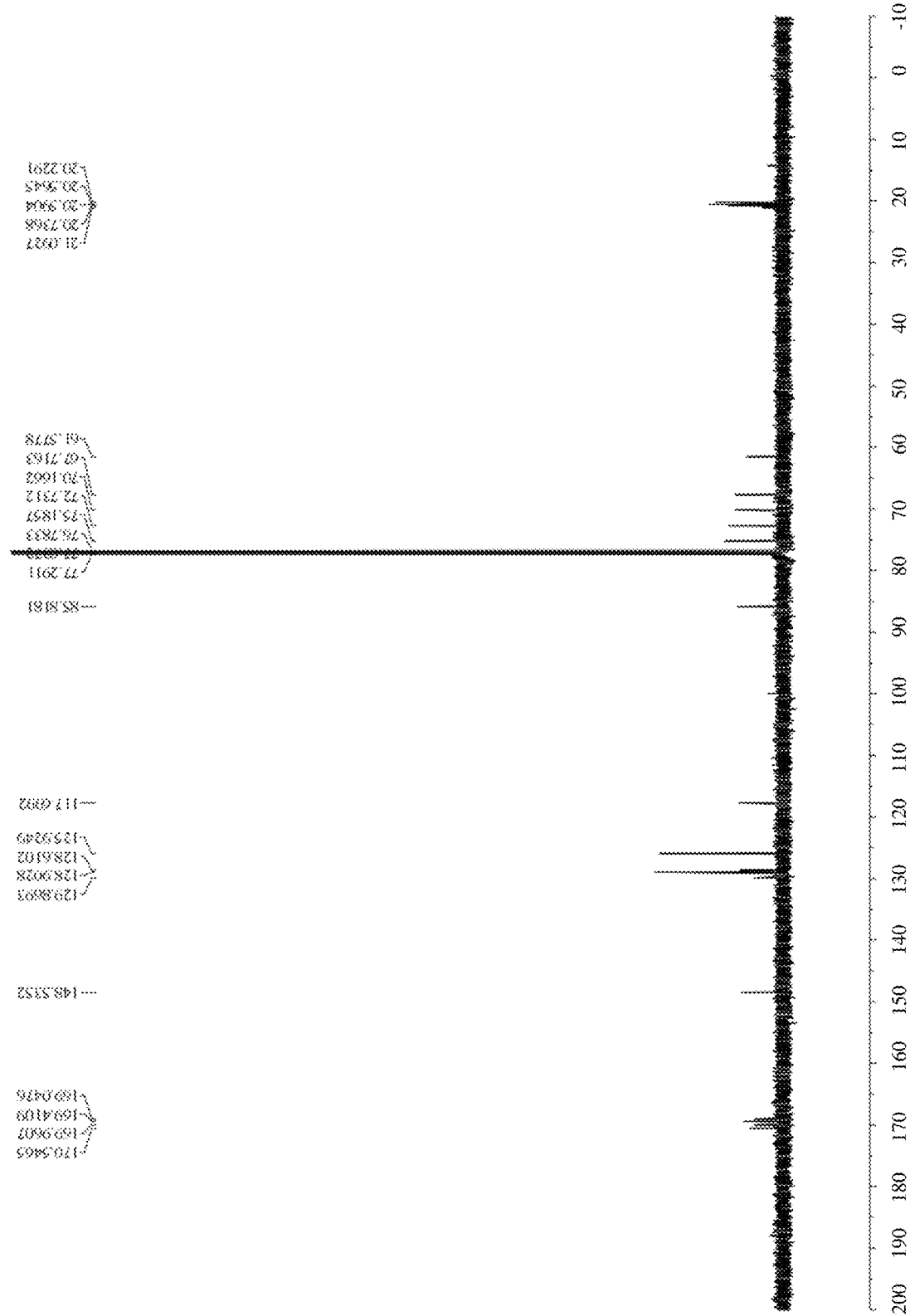
FIG. 20B is a $^{13}$C NMR spectra of the (2S,3R,4R,5S,6R)-2-(acetoxymethyl)-6-(4-phenyl-1H-1,2,3-triazol-1-yl)tetrahydro-2H-pyran-3,4,5-triyl triacetate of FIG. 20A.
Figure 21A:
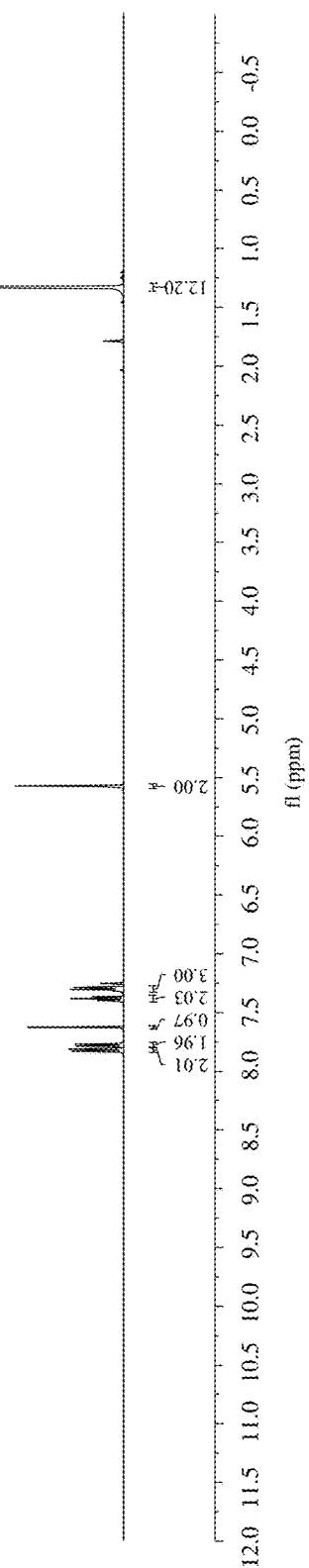
FIG. 21A is a $^1$H NMR spectra of 4-phenyl-1-(4-(4,4,5,5-tetramethyl-1,3,2-dioxaborolan-2-yl)benzyl)-1H-1,2,3-triazole made by a method in accordance with embodiments of the disclosure.
Figure 21A:
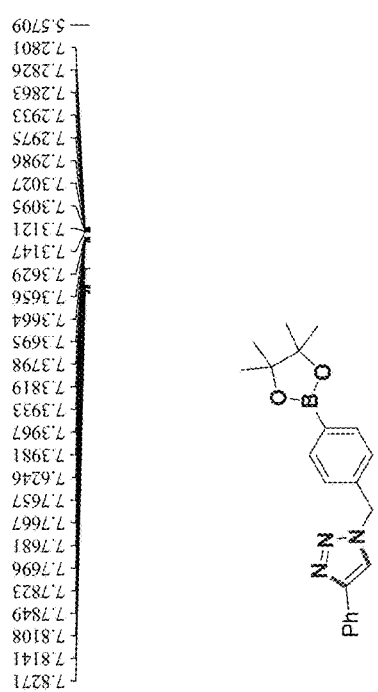
Figure 21B:
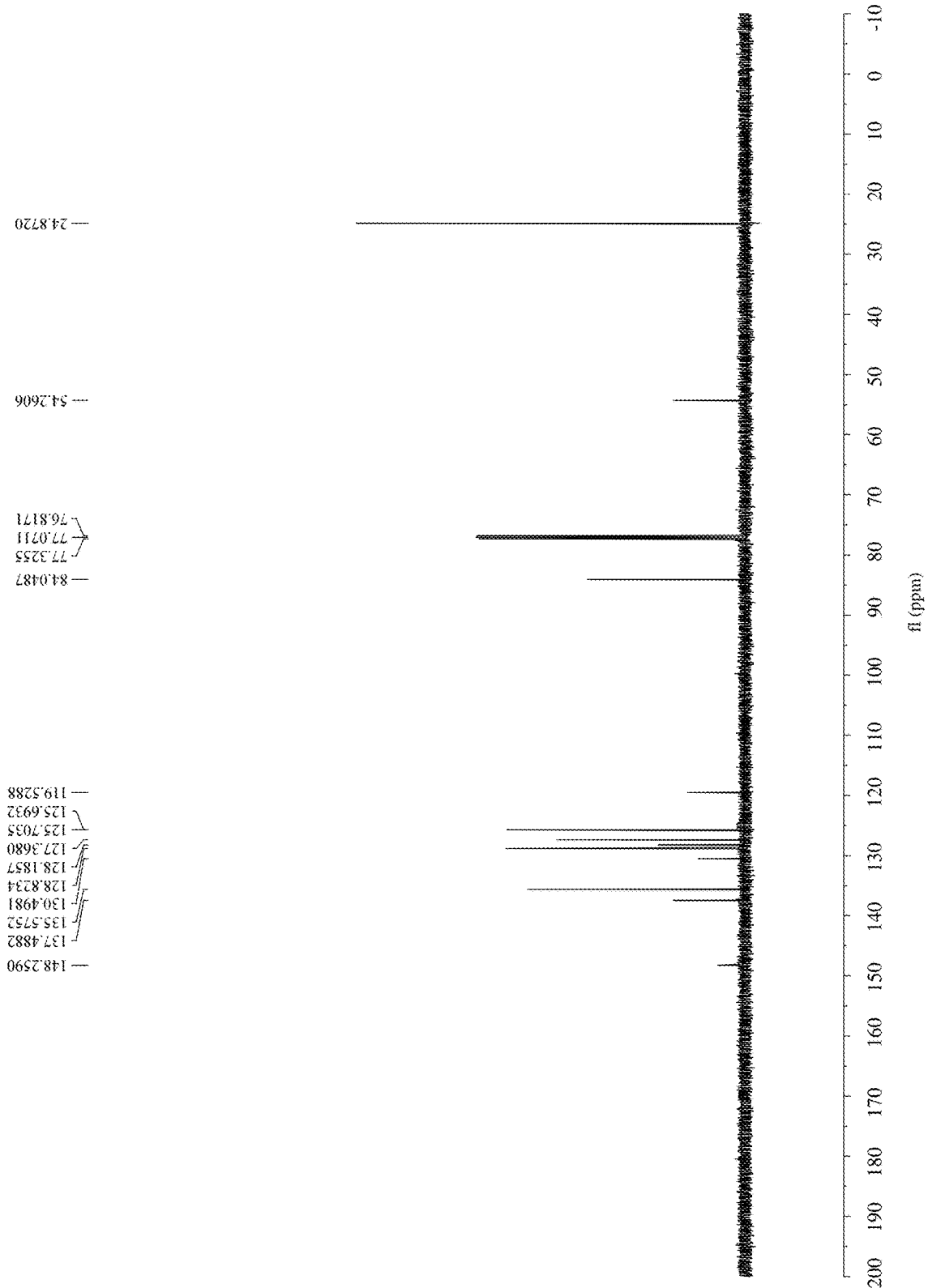
FIG. 21B is a $^{13}$C NMR spectra of the 4-phenyl-1-(4-(4,4,5,5-tetramethyl-1,3,2-dioxaborolan-2-yl)benzyl)-1H-1,2,3-triazole of FIG. 21A.

Referring to FIG. 12A, the Au 4f region show metallic gold feature and it did not change before and after the reaction. This is consistent with the gold being inert in this reaction.

Figure 7C:
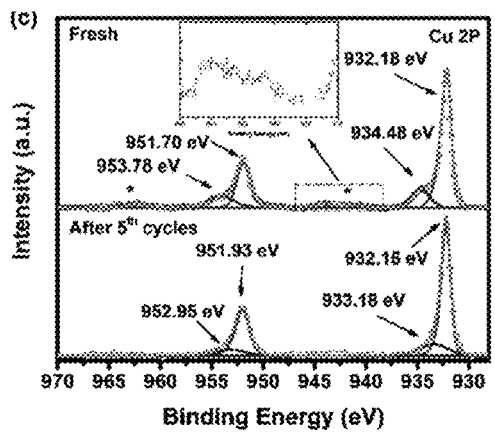
FIG. 7C is a graph showing the XPS results of FIG. 7A in the Cu 2p region. In the graph * indicate the satellite peak of Cu(II) species.
Figure 7D:
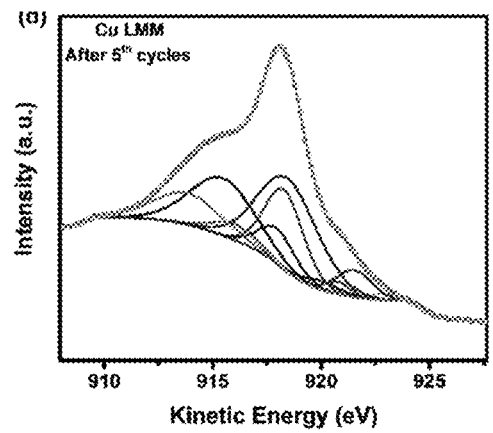
FIG. 7D is a graph showing the XPS results of FIG. 7A in the Cu LMM region for the sample after CuAAC reaction.

Referring to FIG. 7C, in the Cu 2p region, the primary peak at 932.18 eV remained intact after the reaction. This peak can be associated with either Cu(I) or Cu(0). Before the reaction, there was a small amount of Cu(II) on the surface of the nanowires. The primary peak at 934.48 eV and the shape of the shakeup satellite region shown in the inset of FIG. 7C indicate that it is in the form of Cu(OH)$_2$, some of which also reacted with CO$_2$ in the ambient environment to form metal carbonate. Referring to FIGS. 7B and 12B, this was confirmed by the existence of O═C—O (288.55 eV) in C 1s spectra and O 1s region of the freshly prepared AuCu nanowire membrane. After the reaction, the Cu(OH)$_2$ peak, along with the Cu(II) satellite peaks, decreased significantly There was also a significant reduction of the O═C—O (288.55 eV) in C 1s spectra. All of these changes confirmed the dissolution of the Cu(II) hydroxide and carbonate after the reaction. Thus, the dissolved Cu species detected by ICP-MS is likely Cu(II) species, which is why it does not catalyze the CuAAC reaction, as show in in FIG. 6B. The only remaining small peak after the reaction at 933.18 eV can be assigned to CuO, which could come from small oxidation of the sample in air during reaction or sample processing. Referring to FIG. 7D and the table below, without much interference of Cu(II) signal, X-ray excited Cu LMM auger spectrum from the after-reaction sample was deconvoluted into contributions from both Cu(0) and Cu(I).

| Content | Position | FWHM | Raw Area | % At Conc. |
|---|---|---|---|---|
| Cu(0) | 922.85 | 1.21 | 83.3155 | 0.78 |
| Cu(0) | 920.77 | 1.37 | 182.527 | 1.72 |
| Cu(0) | 920.00 | 2.06 | 199.902 | 1.88 |
| Cu(0) | 918.29 | 2.11 | 1804.34 | 16.95 |
| Cu(0) | 916.00 | 2.39 | 416.337 | 3.91 |
| Cu(0) | 915.46 | 3.50 | 2164.75 | 20.33 |
| Cu(I) | 921.51 | 1.91 | 557.834 | 5.24 |
| Cu(I) | 918.46 | 3.23 | 3262.36 | 30.65 |
| Cu(I) | 917.96 | 2.02 | 762.341 | 7.16 |
| Cu(I) | 913.3 | 3.55 | 1209.84 | 11.36 |

Total integration = Cu(0):Cu(I) = 45.6:54.4

The quantitative results showed, within the X-ray penetration depth, the surface of the nanowire after the CuAAC reaction was a mixture of 54% Cu(I) and 46% Cu(0). By comparing the change in the XPS data on the membrane before and after the CuAAC reaction, it was shown that the as-prepared AuCu surface most likely consisted of both Cu(II) oxide (in the form of $Cu(OH)_2$ and $CuCO_3$) and Cu(I) oxide. During the catalytic reaction, the Cu(II) oxide species were dissolved into the reaction medium, exposing $Cu_2O$, which catalyzes the reaction. Because the catalytic experiments were carried out in air, part of the $Cu_2O$ slowly oxidized further into CuO, which is not a catalytically active species. Without intending to be bound by theory, it is believed that this may have contributed to the slow decrease of activity during consecutive cycles.

The use of the "a" or "an" are employed to describe elements and components of the embodiments herein. This is done merely for convenience and to give a general sense of the description. This description should be read to include one or at least one and the singular also includes the plural unless it is obvious that it is meant otherwise.

Still further, the figures depict embodiments for purposes of illustration only. One of ordinary skill in the art will readily recognize from the following discussion that alternative embodiments of the structures and methods illustrated herein may be employed without departing from the principles described herein.

Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed:

1. A membrane for a catalyzing flow reactor, comprising: metal-containing or metal-alloy containing nanowires self-assembled into a porous nanostructure, wherein the porous nanostructure has a thickness of about 10 nm to about 1 cm, and the nanowires have a diameter of about 1 nm to about 500 nm, and an aspect ratio of about 10 to about 100,000, wherein the metal-containing or metal-alloy containing nanowires each comprises an exterior surface arranged so that the metal or metal alloy of the metal-containing or metal-alloy containing nanowires is exposed to one or more reactants during flow of the reactants through the membrane to catalyze a reaction of the one or more reactants through contact with the exposed metal or metal-alloy during flow-through of the reactants through the membrane.

2. The membrane of claim 1, wherein the nanowires comprise gold-copper alloy.

3. The membrane of claim 2, wherein the Au/Cu molar ratio is about 1:4 to about 4:1.

4. The membrane of claim 1, wherein the nanowires comprise one or more of Cu, Ag, Au, Ru, Rh, Pd, Os, Ir, Pt, Sc, Ti, V, Cr, Mn, Fe, Co, Ni, Zn, Y, Zr, Nb, Mo, Tc, Cd, Hf, Ta, W, Re, Os, Ir, La, Ce, Pr, Nd, Pm, Sm, Eu, Gd, Tb, and combinations thereof, and alloys thereof.

5. The membrane of claim 1, where the nanowires comprise one or more of metal carbides, metal nitrides, metal chalcogenides, and metal oxides.

6. The membrane of claim 1, wherein the nanostructure comprises a stacked structure of at least two layers of nanowires.

7. The membrane of claim 1, wherein the nanostructure has a porosity of about 20% to about 80%.

8. The membrane of claim 1, wherein the nanowires have a branched and/or fractal structure.

9. A method of catalyzing a reaction under flow conditions, comprising:
flowing a solution comprising one or more reactants through the membrane of claim 1 under a pressure of less than 10 bar and under conditions sufficient to catalyze a reaction of the one or more reactants.

10. The method of claim 9, wherein the pressure is less than 1 bar.

11. The method of claim 9, wherein the one or more reactants comprise an azide and an alkyne or wherein the one or more reactants comprises 4-nitrophenol, the method being performed under conditions suitable to reduce the 4-nitrophenol to 4-aminophenol.

12. The method of claim 11, wherein the alkyne is one or more of 9-ethynylphenanthrene, 3-phenyl-1-propyne, cyclohexylacetylene, and phenylacetylene; and/or the azide is one or more of benzyl azide and dioxaborolane modified azide.

13. The method of claim 11, wherein the nanostructure comprises copper-gold nanowires.

14. A membrane for a catalyzing flow reactor, comprising: nanowires self-assembled into a porous nanostructure, wherein the nanowires comprise copper, the porous nanostructure has a thickness of about 10 nm to about 1 cm, and the nanowires have a diameter of about 1 nm to about 500 nm, and an aspect ratio of about 10 to about 100,000, wherein the nanowires each comprises one or more copper species arranged on an exterior surface such that the one or more copper species are exposed to one or more reactants during flow of the reactants through the membrane to catalyze a reaction of the one or more reactants through contact with the exposed metal or metal-alloy during flow-through of the reactants through the membrane.

* * * * *